(12) United States Patent
Farrell

(10) Patent No.: US 8,920,163 B2
(45) Date of Patent: *Dec. 30, 2014

(54) ORTHODONTIC APPLIANCE

(71) Applicant: Christopher John Farrell, Helensvale (AU)

(72) Inventor: Christopher John Farrell, Helensvale (AU)

(*) Notice: Subject to any disclaimer, the term of this patent is extended or adjusted under 35 U.S.C. 154(b) by 0 days.

This patent is subject to a terminal disclaimer.

(21) Appl. No.: 13/889,695

(22) Filed: May 8, 2013

(65) Prior Publication Data

US 2013/0244195 A1 Sep. 19, 2013

Related U.S. Application Data

(63) Continuation-in-part of application No. 13/362,584, filed on Jan. 31, 2012, now Pat. No. 8,459,987, which is a continuation of application No. 12/657,488, filed on Jan. 20, 2010, now Pat. No. 8,105,079, which is a continuation-in-part of application No. 11/787,661, filed on Apr. 16, 2007, now abandoned, which is a continuation-in-part of application No. PCT/AU2005/001598, filed on Oct. 14, 2005.

(30) Foreign Application Priority Data

Oct. 14, 2004 (AU) .................................. 2004905924

(51) Int. Cl.
*A61C 7/08* (2006.01)
*A61F 5/56* (2006.01)
*A63B 71/08* (2006.01)

(52) U.S. Cl.
CPC . *A61C 7/08* (2013.01); *A61F 5/566* (2013.01); *A63B 71/085* (2013.01)

USPC .............................................................. 433/6

(58) Field of Classification Search
USPC ....................................... 433/6; 128/861, 862
See application file for complete search history.

(56) References Cited

U.S. PATENT DOCUMENTS

| 2,827,899 A | 3/1958 | Altieri |
| 3,224,443 A | 12/1965 | Monaghan |
| 4,793,803 A | 12/1988 | Martz |
| 5,031,638 A | 7/1991 | Castaldi |
| 5,082,007 A | 1/1992 | Adell |

(Continued)

FOREIGN PATENT DOCUMENTS

WO 0035369 A 6/2000

*Primary Examiner* — Ralph Lewis
(74) *Attorney, Agent, or Firm* — Berenato & White, LLC

(57) ABSTRACT

An orthodontic appliance 1 for promoting development of a dental arch form in a patient who has an underdeveloped dental arch form is disclosed. The appliance 1 includes an arch-shaped base member 2 that is made of a resiliently flexible material, and a teeth engaging member 5 that encloses at least part of the base member 2. The teeth engaging member 5 defines upper and/or lower dental arch receiving channels 46, 47 and is made of a resiliently flexible material that is softer than the base member and is deformable. The appliance 1 has a resting form in which the resilient materials of the base member 2 and the teeth engaging member 5 are in their resting condition. The appliance 1 can be flexed or deformed out of the resting form to fit the underdeveloped dental arch form into the dental arch receiving channel 46, 47. When deformed the appliance 1 exerts a return force that is directed to returning it to its resting form which in use urges the underdeveloped dental arch to expand into a developed dental arch form.

20 Claims, 16 Drawing Sheets

(56) References Cited

U.S. PATENT DOCUMENTS

| | | | |
|---|---|---|---|
| 5,203,695 A * | 4/1993 | Bergersen | 433/6 |
| 5,259,762 A | 11/1993 | Farrell | |
| 5,293,880 A | 3/1994 | Levitt | |
| 5,406,962 A | 4/1995 | Adell | |
| 5,511,562 A | 4/1996 | Hancock | |
| 5,865,619 A | 2/1999 | Cross, III et al. | |
| 6,082,363 A | 7/2000 | Washburn | |
| 6,508,251 B2 | 1/2003 | Kittelsen et al. | |
| 6,539,943 B1 | 4/2003 | Kittelsen et al. | |
| 6,584,978 B1 | 7/2003 | Brett et al. | |
| 6,598,605 B1 | 7/2003 | Kittelsen et al. | |
| 7,210,483 B1 | 5/2007 | Lesniak et al. | |
| 8,105,079 B2 | 1/2012 | Farrell | |
| 2003/0019497 A1 | 1/2003 | Farrell | |
| 2003/0101999 A1 | 6/2003 | Kittelsen et al. | |
| 2003/0219690 A1 | 11/2003 | Graham | |
| 2004/0103905 A1 | 6/2004 | Farrell | |
| 2004/0154625 A1 | 8/2004 | Foley | |
| 2004/0154626 A1 | 8/2004 | Washburn et al. | |
| 2005/0115571 A1 | 6/2005 | Jacobs | |
| 2006/0065277 A1 | 3/2006 | Jacobs | |
| 2006/0084024 A1 | 4/2006 | Farrell | |
| 2006/0219250 A1 | 10/2006 | Farrell | |

* cited by examiner ved ORTHODONTIC APPLIANCE

This application is a continuation-in-part of U.S. application Ser. No. 13/362,584, filed Jan. 31, 2012, which is a continuation of U.S. application Ser. No. 12/657,488, filed Jan. 20, 2010, which was a continuation-in-part of U.S. application Ser. No. 11/787,661, filed 16 Apr. 2007, now abandoned, which was a continuation-in-part of PCT/AU05/01598, filed on 14 Oct. 2005, which designated the United States, now lapsed, which claimed priority to AU 2004 905924 filed on 14 Oct. 2004.

FIELD OF THE INVENTION

This invention relates to an orthodontic appliance for use in orthodontic treatment.

This invention relates particularly but not exclusively to an active orthodontic appliance for promoting expansion of an underdeveloped upper dental arch and alignment of teeth on the upper dental arch. It will therefore be convenient to hereinafter describe the invention with reference to the treatment of a Class 2 malocclusion. However it is to be clearly understood that the invention is capable of broader application and can be used for the treatment of other conditions.

DEFINITIONS

In this specification the term "engaging" shall bear a broad meaning and shall not be limited to a retaining or latching engagement. Similarly the term "flange" shall bear a broad meaning and shall not be limited to a radially extending wall at the end of a cylindrical section. It shall be understood to include a wall or wall like formation that extends transversely away from another surface, e.g. a web surface.

The term "comprising" shall be understood to have a broad meaning similar to the term "including" and will be understood to imply the inclusion of a stated integer or step or group of integers or steps but not the exclusion of any other integer or step or group of integers or steps. This definition also applies to variations on the term "comprising" such as "comprise" and "comprises".

In this specification the term "correct dental occlusion" shall bear a broad meaning and shall refer to an occlusion where the dentition of the upper and the lower arches come together in a correct positioning relative to each other along the length of the arch. Similarly the term "dental arch and associated dental structures" shall include the bone of the dental arch, the surrounding bony gum tissues, the soft gum tissues and also the dentition on the arch.

Further in this specification the terms "frame", "frame structure" and open frame structure" shall be interpreted broadly and shall include all frames. Further the terms may be used interchangeably in this specification.

Further in this specification the terms "inner wall" and "outer wall" shall be used interchangeably with the terms "inner flange" and outer flange". Further the terms "inner flange" and outer flange" shall be interpreted broadly.

BACKGROUND TO THE INVENTION

One type of orthodontic appliance that is known is a custom made retainer or plate appliance that is moulded from bite impressions of a particular patient. The bite impressions are used to make laboratory models of a particular patient's arches and associated dental structures which are then used to mould a customised retainer appliance for fitting that particular patient. A limitation of the retainer appliances is that the cost of producing them is high because they are individually made for each patient.

Orthodontic systems using fixed appliances that are commonly called orthodontic braces are also used for orthodontic treatment. Orthodontic braces comprise a plurality of brackets or bands each of which is mounted over an individual tooth and bonded thereto so that it is permanently mounted on the tooth. The brackets are linked together by means of a wire that passes through wire apertures formed in each of the brackets. The wire applies a force to the brackets that can then be used to reposition and align the teeth on the dental arch. In particular these fixed appliances can be used to bring the anterior teeth on the upper and lower arches in the correct relative position to each other. The wire can progressively be drawn in to retract the incisor teeth on the anterior region of the upper dental arch to "close" an "open" bite. The fixed appliances can achieve some degree of arch expansion together with alignment of the teeth but the extent of the expansion is limited. The fixed appliances use brackets to move teeth on a dental arch, and in particular to align the teeth. For example these fixed appliances can be used to retract protruding teeth, in particular protruding incisors on the upper arch of a user, and they can also be used to advance retruded teeth.

The fixed braces described above have their drawbacks. Firstly Applicant's experience is that most orthodontic patients would choose not to wear braces if an alternative treatment was available. The brackets of the braces are generally unsightly and detract from the patient's looks while the braces are being worn, e.g. for the duration of the treatment. Secondly the braces can be uncomfortable to wear and can cause trauma, such as cuts and bruises to the intraoral soft tissues of a user. The soft buccal mucosa is particularly susceptible to injury from projections on the buccal surface of the brackets. Thirdly the brackets and wire are fixed on the teeth of a patient by an orthodontist and they cannot be removed by the patient. Fourth another shortcoming that has plagued the use of braces is patient relapse where the teeth move back towards their original positions once the brackets are removed. The braces are non-removable appliances that cannot be used on an intermittent basis like a removable plate retainer. The appliance is an active appliance that ceases to have any influence once it is removed.

Aside from the traditional orthodontic treatments described above, in more recent times some treatments have focused on encouraging and promoting improved oral habits as a way of developing an intra-oral environment that is less likely to develop severe class 2 and class 3 malocclusions. The applicant has developed an arch shaped appliance that can train a patient to position certain key intraoral structures such as the tongue in the correct position and to resist the development of malocclusions caused by poor oral habits. One such feature is a tongue tab that assists in positioning the tongue at the correct height and reduces tongue thrusting.

It would be advantageous if a removable orthodontic appliance could be devised that at least ameliorated one or more of the shortcomings of the appliances and treatments described above.

SUMMARY OF THE INVENTION

According to one aspect of this invention there is provided an orthodontic appliance for developing a dental arch form and alignment of teeth on a patient, the orthodontic appliance comprising:

a resiliently deformable teeth engaging member that includes an arch-shaped web that defines upper and lower occlusal bite surfaces, the teeth engaging member has inner and outer walls that project transversely away from the upper surface of the web, and the web and the inner and outer flanges define an upper arch receiving channel within which an upper dental arch and associated dentition of a patient can be received; and at least one complementary pair of upper arch teeth positioning formations on the teeth engaging member projecting into the upper arch receiving channel for expanding the arch and positioning individual teeth along the upper arch, wherein the appliance has a resting form and can be deformed out of the resting form when fitted to a patient to receive a patient's upper arch in the upper arch receiving channel, and exert a return force against the received arch to develop the arch form.

Each complementary pair of upper arch teeth positioning formations may comprise an outer teeth positioning formation projecting into the upper arch receiving channel from the outer wall and an inner teeth positioning formation projecting into the upper arch receiving channel from the inner wall.

The appliance may be an active appliance. Further each of the upper arch teeth positioning formations may be resiliently deformable.

Each complementary pair of upper arch teeth positioning formations may be located at a predetermined position along the arch form so as to project into a space between two specific adjacent teeth, and the outer and inner teeth positioning formations of each complementary pair may be aligned with each other in a direction transverse to the line of the arch form. This way the teeth positioning formations of each complementary pair project into the same space between two specific adjacent teeth.

Each upper arch teeth positioning formation may comprise a wedge formation and the wedge formation may be substantially vertically extending. Further the wedge formation may include a wedge base on the inner or outer wall and a wedge apex that projects away from the wedge base into the upper arch receiving channel.

Each wedge formation on the inner wall may extend from the web up more than half of the height of the inner wall, e.g. substantially the full height of the inner wall. Further each wedge formation on the inner wall may extend up from the web more than half of the height of the outer wall, e.g. substantially the full height of the inner wall.

The teeth engaging member including the inner and outer walls may be integrally formed of a resiliently deformable material, and each wedge formation may be integrally formed with the associated inner or outer wall of the teeth engaging member of a resiliently deformable material. The teeth engaging member may be integrally formed by a moulding operation, e.g. an injection moulding of silicon rubber and each wedge formation may be integrally formed with the associated wall in the moulding operation and be moulded of silicon rubber.

The teeth engaging formation may include a plurality of said complementary pairs of upper arch teeth positioning formations. The plurality of complementary pairs may be arranged to be bilaterally symmetrical on the teeth engaging member.

Further the plurality of complementary pairs of upper arch teeth positioning formations may include two pairs of complementary teeth positioning formations positioned on either side of a midline of the appliance for projecting into an interproximal space between the inner and outer incisors on the left and right sides. Further the plurality of complementary pairs of upper arch teeth positioning formations may include two pairs of complementary teeth positioning formations positioned on either side of a midline of the appliance for projecting into an interproximal space between the outer incisors and the canines on the left and right sides.

Further the plurality of complementary pairs of upper arch teeth positioning formations may include two pairs of complementary teeth positioning formations positioned on either side of a midline of the appliance for projecting into an interproximal space between the canines and the pre-molars on the left and right sides. Further the plurality of complementary pairs of upper arch teeth positioning formations may include two pairs of complementary teeth positioning formations that are positioned on either side of a midline of the appliance for projecting into an interproximal space between the pre-molars and adjacent molars on the left and right sides of the patient. Further the plurality of complementary pairs of upper arch teeth positioning formations may include two pairs of complementary teeth positioning formations positioned on either side of a midline of the appliance for projecting into an interproximal space between two adjacent teeth on the left side and the corresponding two adjacent teeth on the right side of the patient.

The plurality of complementary pairs of upper arch teeth positioning formations may include one complementary pair of teeth engaging formations that is positioned on the midline of the appliance for projecting into an interproximal space between the left and right inner incisors on the patient.

The inner and outer walls may project transversely away from the lower surface of the web, and the web and the inner and outer walls may define a lower arch receiving channel within which a lower dental arch and associated dentition of a patient can be received. The appliance may further include at least one complementary pair of lower arch teeth positioning formations on the teeth engaging member projecting into the lower arch receiving channel for expanding the lower arch and positioning individual teeth along the lower arch.

Each complementary pair of lower arch teeth positioning formations may comprise an outer teeth positioning formation projecting into the lower arch receiving channel from the outer wall and an inner teeth positioning formation projecting into the lower arch receiving channel from the inner wall.

Each complementary pair of lower arch teeth positioning formations may be located at a predetermined position along the arch form so as to project into a space between two specific adjacent teeth. Further the outer and inner teeth positioning formations of each complementary pair may be aligned with each other in a direction transverse to the line of the arch form.

Each lower arch teeth positioning formation may comprise a wedge formation that is substantially vertically extending. The wedge may include a wedge base on the inner or outer wall and a wedge apex that projects away from the wedge base into the lower arch receiving channel.

Each wedge formation on the lower arch teeth positioning formations may be integrally formed with the associated inner or outer wall of the teeth engaging member, e.g. the wedge formation may be integrally moulded with the associated wall and the remainder of the teeth engaging member, of the same material as the wall.

The appliance may include a plurality of complementary pairs of lower arch teeth positioning formations, and the plurality of complementary pairs may be arranged to be bilaterally symmetrical on the teeth engaging member. Further each of the lower arch teeth positioning formations may be resiliently deformable.

For example the plurality of complementary pairs of lower arch teeth positioning formations may include two pairs of complementary teeth positioning formations that are positioned on either side of a midline of the appliance so as to project into the interproximal space between the inner and outer incisors on the left and right sides of the patient. Further the plurality of complementary pairs may include one complementary pair that is positioned on the midline of the appliance so as to project into the interproximal space between the left and right inner incisors on the patient.

Further the plurality of complementary pairs of lower arch teeth positioning formations may include two pairs of complementary lower teeth positioning formations that are positioned on either side of a midline of the appliance so as to project into the interproximal space between the outer incisors and the canines on the left and right sides of the patient. Further the plurality of complementary pairs of lower arch teeth positioning formations may include two pairs of complementary teeth positioning formations that are positioned on either side of a midline of the appliance so as to project into the interproximal space between the canines and the pre-molars on the left and right sides of the patient. Yet further the plurality of complementary pairs of lower arch teeth positioning formations may include two pairs of complementary teeth positioning formations that are positioned on either side of a midline of the appliance so as to project into the interproximal space between the pre-molars and adjacent molars on the left and right sides of the patient The plurality of complementary pairs of lower arch teeth positioning formations may include two pairs of complementary teeth positioning formations that are positioned on either side of a midline of the appliance so as to project into an interproximal space between two adjacent teeth on the left side and the corresponding two adjacent teeth on the right side of the patient.

The appliance may further include an arch-shaped base member that is received within and is substantially enclosed by the teeth engaging member. The base member may be formed from a resiliently deformable material having a greater hardness and rigidity than the teeth engaging member so that the base member contributes to the resting form return force for driving expansion of the patient's arch.

The base member may include a substantially planar frame extending parallel to the web. The frame of the base member may include an arch-shaped outer frame member and an arch-shaped inner frame member that are spaced apart from each other and a plurality of transverse frame members that connect the outer frame member and the inner frame member.

The base member may further include an outer teeth repositioning formation, for aligning a row of teeth along the upper dental arch, which projects up above the frame and is received within the outer flange of the teeth engaging member.

The teeth engaging member may be formed of a resiliently deformable material that is softer than the material from which the base member is formed and which provides a soft cushion for forming a cushion for bearing against the dental arch and dental structures of the patient. Further the material of the base member and the material of the teeth engaging member may be selected such that they flex in unison with each other and resist being delaminated.

The appliance may comprise a front region that merges with two opposing arm regions that project away from either side of the front region, and the web may decrease in transverse width in a direction from the arm regions towards the front region so as to correspond with the decrease in width of the occlusal surfaces of a dental arch from a molar region towards an incisor region. The dental arch and dentition may be received within the dental arch receiving channel with a tight fit where the dentition bears against the inner and outer walls of the teeth engaging member.

According to another aspect of this invention there is provided a method of orthodontic treatment of a patient to develop their upper arch, said method including:
providing an orthodontic appliance comprising: a resiliently deformable teeth engaging member that includes an arch-shaped web that defines upper and lower occlusal bite surfaces, the teeth engaging member has inner and outer walls that project transversely away from the upper surface of the web, and the web and the inner and outer flanges define an upper arch receiving channel within which an upper dental arch and associated dentition of a patient can be received; and at least one complementary pair of upper arch teeth positioning formations on the teeth engaging member projecting into the upper arch receiving channel for expanding the arch and positioning individual teeth along the upper arch;
fitting the orthodontic appliance within the mouth of the patient by deforming the orthodontic appliance from a resting form, and mounting the orthodontic appliance over the patient's upper dental arch so that the upper dental arch is received within the upper dental arch receiving channel, and then releasing the deformed appliance so that it exerts a return force against the upper arch of the patient to promote expansion of the arch; and
making the patient wear the orthodontic appliance on a regular basis.

The appliance may include any one or more of the optional or preferred features of the complementary pairs of teeth positioning formations defined in the preceding aspect of the invention above.

The method may include making the patient wear the appliance for at least eight hours on substantially each day over a treatment period of 12 to 24 months.

According to yet another aspect of the invention there is provided an orthodontic appliance for developing a developed dental arch form in a patient who has an underdeveloped dental arch form, the appliance comprising:
an arch-shaped base member that is constructed from a resilient, flexible material; and
a deformable teeth engaging member that substantially encloses at least part of the base member and that defines at least one of an upper or a lower dental arch receiving channel, the teeth engaging member being constructed from a resilient, flexible material that is softer than the resilient, flexible material of the base member,
wherein the appliance has a resting form in which the base member and the teeth engaging member are in their resting condition, and the appliance can be manipulated from the resting form when fitted to a patient to receive the patient's underdeveloped dental arch form in the at least one dental arch receiving channel, and wherein the appliance exerts a resting form return force urging the underdeveloped dental arch form to develop into the developed dental arch form.

The at least one dental arch receiving channel has a shape corresponding to the developed dental arch form when the appliance is in the resting form. The dental arch receiving channel may have a caternary shape representing correct dental occlusion when the appliance is in the resting form.

The appliance may have a resilient flexibility that permits the appliance to be manually flexed or deformed out of the resting form to fit the underdeveloped dental arch into the dental arch receiving channel without excessive effort being required.

The appliance may include a front region that merges with two opposing arm regions that project away from either side of the front region. The front region of the appliance may be less flexible than the arm regions whereby a flexure may be formed at either side of the front region when the arm regions are flexed towards each other.

The material of the base member and the material of the teeth engaging member may be selected so that they flex in unison with each other when they are deformed out of their resting conditions, and also so that the base member and the teeth engaging member resist being delaminated from each other when they are flexed out of their resting conditions.

The teeth engaging member may include an arch-shaped web that defines upper and lower occlusal bite surfaces, and the teeth engaging member may have inner and outer flanges that project transversely away from at least one of an upper or a lower surface of the web, whereby the at least one dental arch receiving channel is defined between the web and the inner and outer flanges.

The web may decrease in transverse width in a direction from the arm regions toward the front region of the appliance so as to correspond with the decrease in width of the occlusal surfaces of a dental arch in a direction from a molar region towards an incisor region, whereby the inner and outer flanges of the teeth engaging member may bear against a patient's dental arch and dental arch structures.

The inner and outer flanges may project away from both the upper and lower surfaces of the web defining both upper and lower dental arch receiving channels within which respective upper and lower dental arches of a patient can be received.

The teeth engaging member may substantially fully enclose the base member. In particular the teeth engaging member may fully encase an outer surface of the base member.

The teeth engaging member may be made from a resiliently elastic material that is selected to be softer than intra-oral soft tissue, whereby to form a soft cushion for bearing against the dental arch and dental structures of a patient. The resilient, flexible material of the teeth engaging member may be silicone rubber, e.g. a medical grade silicone rubber. The silicone rubber cushions the appliance against the dental arch and associated dental structures including teeth, gums and other intra-oral tissues of a user. Instead the resilient, flexible material of the teeth engaging member may be made of a polyvinyl chloride (PVC).

The base member may comprise an open frame structure including an arch-shaped outer frame member and an arch-shaped inner frame member that are spaced apart from each other.

The base member may include a plurality of spaced apart transverse frame members connecting the outer frame member and the inner frame member.

The transverse spacing between the inner and outer frame members may decrease in a direction from the arm regions to the front region of the appliance, whereby an outline of the base member corresponds substantially with that of the web of the teeth engaging member.

The base member may include a first pair of transverse frame members including one transverse frame member towards one side edge of the front region of the appliance and a further transverse frame member towards the other side edge of the front region, wherein the left and right transverse frame members are substantially aligned with respective left and right outer incisors of a patient.

The base member may include a front transverse frame member intermediate the first pair of transverse frame members. The front transverse frame member may be positioned substantially centrally with respect to the base member and may have a centre point midway along its length that is aligned with a midline of the base member. The front transverse frame member may extend across at least part of the two central incisors of a patient when the appliance is fitted to a patient.

The one and further transverse frame members of the first pair may have a width of 1 to 4 mm, e.g. 2 to 3 mm. The front transverse frame member may have a width of 5 to 15 mm (when measured extending from one side edge to the other. For example the front transverse frame member may have a width of 8 to 12 mm.

The base member may further include a second pair of transverse frame members towards the free ends of the base members comprising a left rear transverse frame member towards a free end of an arm region and a right rear transverse frame member towards a free end of the other arm region. Each of the left and right rear transverse frame members may have a width of 2-10 mm, e.g. about 5 mm.

The base member may further include a third pair of transverse frame members positioned intermediate the first and second pairs of transverse frame members. The third pair of transverse frame members may comprise a left transverse frame member positioned intermediate said transverse frame member of the first pair and the left rear transverse frame member, and a right transverse frame member positioned intermediate said right transverse frame member of the first pair and the right rear transverse frame member. The third pair of intermediate transverse frame members may be positioned adjacent to the first premolars on the dental arch when the appliance is fitted to the patient, which are the fourth teeth on the arch located in the first and second quadrants. The third pair of intermediate transverse frame members may be positioned closer to the left and right rear transverse frame members than said left and right transverse frame members of the first pair on the front region of the base member. Each pair of intermediate transverse frame members may be symmetrically arranged on each side of a midline of the base member, e.g. the arrangement of transverse frame members on the base member may be bilaterally symmetrical.

The base member may further include an outer teeth row repositioning formation that projects away from the outer frame member. The outer teeth row repositioning formation may comprise an outer flange that projects up above the open frame structure and extends along the central front region of the appliance and across a patient's upper arch incisor teeth. The outer flange may extend up to a height of 2 to 10 mm above the transverse frame members, e.g. an upper surface of the adjacent or proximate transverse frame members, along the front region of the appliance.

The outer flange may also extend along at least part of the left and right arm regions of the appliance across a patient's molar teeth. The left and right flange arm regions may extend up to a height of 2 to 6 mm above the transverse frame members, e.g. an upper surface of the adjacent or proximate transverse frame members, along the arm regions of the appliance. Optionally the outer flange may comprise a continuous wall that extends in a substantially uninterrupted fashion along the base member and the height of the continuous wall may vary along the length of the wall.

The base member may further include an inner teeth row repositioning formation projecting away from the inner frame member. The inner teeth row repositioning formation may comprise an inner flange that projects up above the open frame structure. The inner flange on the inner frame member may project up to a height of about 1-3 mm, e.g. about 2 mm up from the transverse frame members, e.g. on the upper surface of the adjacent or proximate transverse frame members.

The inner flange may project up above the transverse frame members along at least the front region of the appliance. The inner flange may also project up from the transverse frame members along the arm regions of the appliance. Further the inner flange may have substantially the same height along its full length. The outer and the inner flanges may be formed integrally with the open frame structure, e.g. in an injection moulding operation.

In one form of the invention neither the outer flange on the outer frame member nor the inner flange on the inner frame member extends or depends downwardly below the plane of the open frame to any appreciable extent. However an appliance with one or more downwardly depending flanges is contemplated to be within the scope of the invention. Applicant has found that with the base member materials that he has used, a satisfactory stiffness and strength can be obtained with outer and inner flanges that project up from the open frame but not down from the open frame. However if a greater rigidity is required to be conferred by the base member for the appliance to perform its orthodontic function, then the inner and/or outer flanges could depend downwardly from the open frame as well as projecting upwardly.

In a further alternative the inner and outer flanges described above may project down from the plane of the open frame or the transverse frame members instead of projecting up from the transverse frame members.

The resiliently flexible material of the base member may be a polymeric material that is a polyamide material, for example nylon, or an addition polymer, for example polyethylene or polypropylene, or a condensation polymer, for example polyurethane, or a polycarbonate, or a thermoplastic elastomer, for example santoprene.

The teeth engaging member may include at least one pair of adjacent teeth positioning formations for assisting with the positioning of specific teeth of a patient that are located adjacent to said at least one pair of adjacent teeth positioning formations.

Each teeth positioning formation of said at least one pair of adjacent teeth positioning formations may be aligned with each other along the length of the teeth engaging member and may be located on respectively the inner and outer flanges of the teeth engaging member facing into the associated arch receiving channel, being either the upper arch receiving channel or the lower arch receiving channel.

Each adjacent teeth positioning formation of said at least one pair of adjacent teeth positioning formations may comprise a wedge shaped protrusion having a wedge point facing into the channel away from the flange on which it is located. Further the adjacent teeth positioning formations of each pair may be integrally formed with the flange on which it is located, e.g. by being moulded integrally with the remainder of the teeth engaging member.

The teeth engaging member may include a first pair of said adjacent teeth positioning formations that are arranged on the midline of the appliance for positioning between the two inner incisors when mounted on a patient.

The teeth engaging member may include a second and third pair of adjacent teeth positioning formations that are arranged to be positioned between the inner and outer incisors on the left side, and between the inner and outer incisors on the right side.

The teeth engaging member may include fourth and fifth pairs of adjacent teeth positioning formations that are arranged to be positioned between the outermost incisor and the canine on the left side, and the outermost incisor and the canine on the right side of the arch of a patient.

The teeth engaging member may include sixth and seventh pairs of adjacent teeth positioning formations that are arranged to be positioned between the canine and the first pre-molar on the left side, and the canine and the first pre-molar on the right side of the arch of a patient. The teeth engaging member may include yet further pairs of adjacent teeth positioning formations for positioning further teeth on the arch of a user.

In those forms of the invention where the teeth engaging member defines both upper and lower channels for receiving the upper and lower dental arches and associated dental structures of a patient, the teeth engaging member may have pairs of adjacent teeth positioning formations in both said upper and lower channels for positioning specific teeth on both the upper and lower arch of the patient.

The orthodontic appliance may also include a tongue tab for encouraging a patient to correctly position their tongue. The tongue tab may be formed on the inner flange of the teeth engaging member and may be positioned above the web.

The teeth engaging member may include at least one cutaway or recess above the web on the inner flange of the teeth engaging member. Conveniently the inner flange may define two cutaways above the web on the inner flange, namely one on either side of the tongue tab. The teeth engaging member may include at least one further cutaway or recess below the web on the inner flange of the teeth engaging member. The further cutaway may be defined on the midline of the appliance. The one and further cutaways enable the teeth engaging member provide space when the left and arm regions of the appliance are moved towards each other when the appliance is manually flexed out of its resting form and thereby assist with manipulation of the appliance.

The teeth engaging member may include a cut away on the outer flange above the web, and another cutaway on the outer flange below the web. These cutaways are formed in the outer flange so that an underlying region of the soft gum on the associated dental arch of a patient does not make contact with the teeth engaging member when the appliance is mounted on the patient in use.

The web of the teeth engaging member appliance may be formed of varying thickness along its length. In particular the thickness of the web may increase progressively in a direction rearward from the central front region of the appliance up to respective points of maximum thickness that are positioned forward of the free end of the arm regions. The thickness of the web increases up to the respective points of maximum thickness on each arm region, and thereafter the thickness of the teeth engaging member progressively decreases towards the respective free ends of the arm regions. The thickening of the teeth engaging member may resemble an inverted aerofoil, e.g. with a curved lower surface and a substantially planar upper surface, when viewed in cross section. By shaping the web region in this way, the teeth engaging member supports the dentition on the upper and lower arches when the upper and lower jaws are brought together.

This encourages relaxation of the muscles, particularly where the user has a malocclusion and there is a space between the occlusal surfaces of the dentition on the upper and lower arches. It also supports the temporomandibular joint (TMJ joint).

In one example form of the invention the base member may be constructed from nylon and the teeth engaging member from silicon rubber. In another example form the base member may be of nylon and the teeth engaging member may be PVC.

Applicant envisages that the orthodontic appliance will be made in several sizes and a suitable size of appliance will be selected for a patient based on the size of their dental arches and associated dental structures. Applicant envisages that the appliance will be manufactured in three or more different arch sizes to accommodate relatively larger arch sizes in patients and relatively smaller arch sizes. Each arch size will be manufactured with six or more variations in the arrangements of the adjacent teeth positioning formations. The different arrangements of the adjacent teeth positioning formations are intended to cater for different teeth sizes and different individual teeth positions in different patients.

According to another aspect of this invention there is provided an orthodontic appliance for developing a dental arch form in a patient who has an underdeveloped arch form, the appliance comprising:

an arch-shaped base member that is constructed from a resilient, flexible material having a shape that corresponds generally to a dental arch form; and a deformable teeth engaging member that substantially encloses at least part of the base member and that defines at least one of an upper or a lower dental arch receiving channel, the teeth engaging member being constructed of a resilient, flexible material that is more flexible than the resilient, flexible material of the base member, wherein the appliance comprises a front region that merges with two opposing arm regions that project away from either side of the front region, and the front region is constructed with a greater stiffness than the arm regions, and the appliance has a resting form in which the base member and the teeth engaging member are in their resting condition, and wherein the appliance can be manipulated out of the resting form when fitted to a patient to receive the patient's underdeveloped dental arch form in the at least one dental arch receiving channel, and wherein the front region, due to said greater stiffness, exerts a greater resting form return force against the patient's underdeveloped dental arch form than the arm regions, urging the underdeveloped dental arch form to develop into the developed dental arch form.

The greater resting form return force applied by the front region against the corresponding region of the patient's arch form in particular encourages this region of the arch form to develop, i.e. it encourages expansion of an anterior region of the patient's arch form.

The base member may be in the form of an open frame structure comprising an arch-shaped outer frame member and an arch-shaped inner frame member, and the front region of the appliance may be formed with a greater stiffness that the left and right arm regions thereof by having at least one transverse frame member extending between the inner and outer frame members in said front region.

The appliance and the base member may include any one or more of the features of the appliance and/or base member defined in the preceding aspects of the invention.

This invention also extends to a method of treating a patient to develop an underdeveloped arch form in a patient into a developed arch form, the method comprising the steps of fitting an appliance as described in the first or second aspects of the invention above to a patient, and having the patient wear the appliance on a regular basis.

The method may include encouraging development of the upper arch of a patient by expanding the upper arch form to treat a Class 2 malocclusion.

The method may include aligning the dentition on the underdeveloped dental arch of the patient that is being developed into a developed arch form.

Having the patient wear the appliance may include having the patient wear the appliance for at least 12 hours in each 24 hour day. Preferably the patient wears the appliance at least 2 hours during the day time and during the night while the patient is sleeping.

DETAILED DESCRIPTION OF THE INVENTION

An orthodontic appliance in accordance with this invention may manifest itself in a variety of forms. It will be convenient to hereinafter provide a detailed description of at least one embodiment of the invention with reference to the accompanying drawings. The purpose of providing this detailed description is to instruct persons having an interest in the subject matter of the invention how to put the invention into practice. It is to be clearly understood however that the specific nature of this detailed description does not supersede the generality of the preceding statements. In the drawings:

Figure 1:
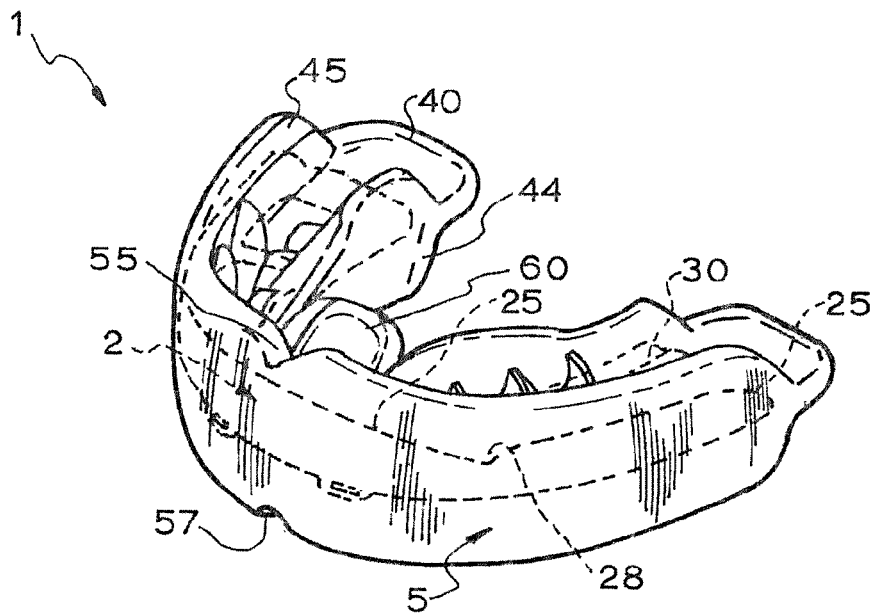
FIG. 1 is an upper three dimensional view of an orthodontic appliance that is an orthodontic appliance in accordance with one embodiment of the invention, viewed from the front.
Figure 2:
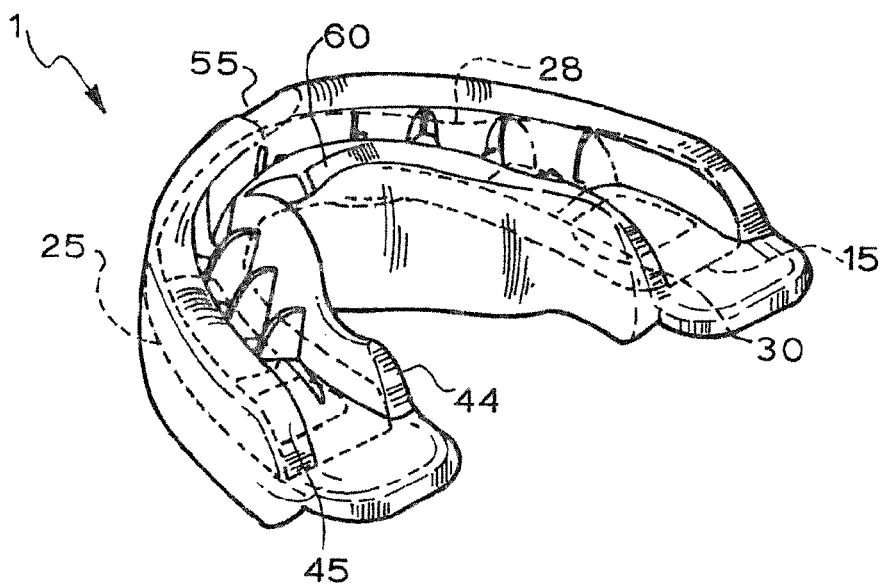
FIG. 2 is an upper rear three dimensional view of the appliance of FIG. 1, viewed from the rear.
Figure 3:
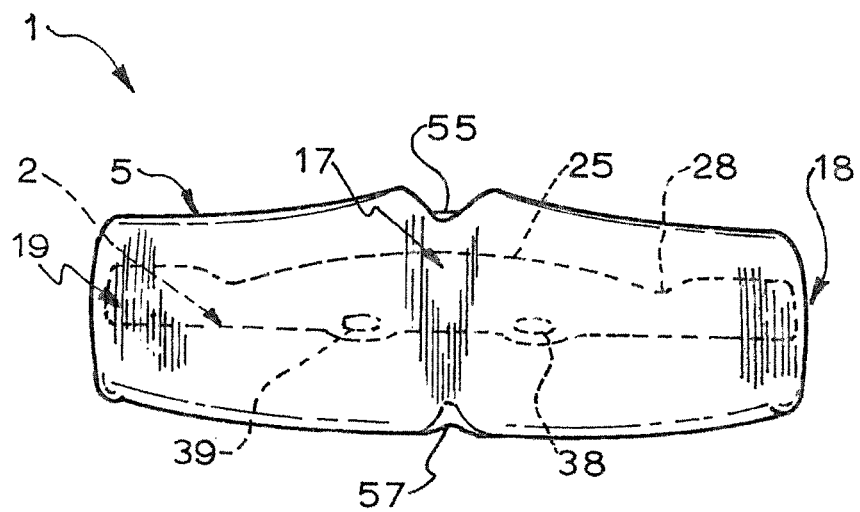
FIG. 3 is a front view of the appliance of FIG. 1.
Figure 4:
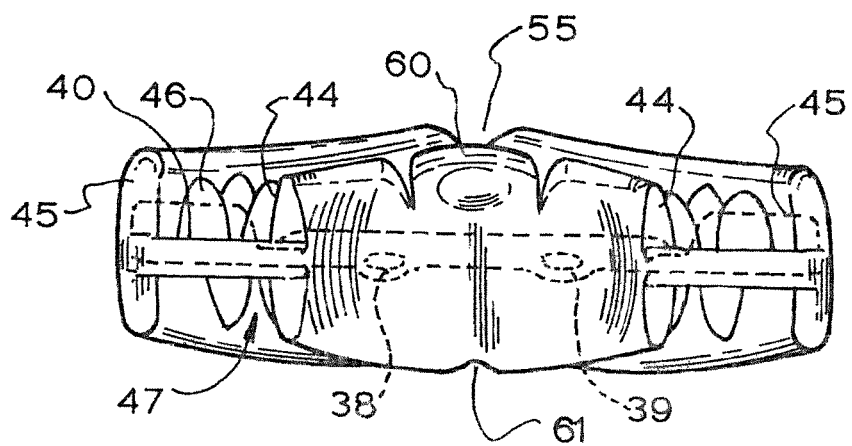
FIG. 4 is a rear view of the appliance of FIG. 1.
Figure 5:
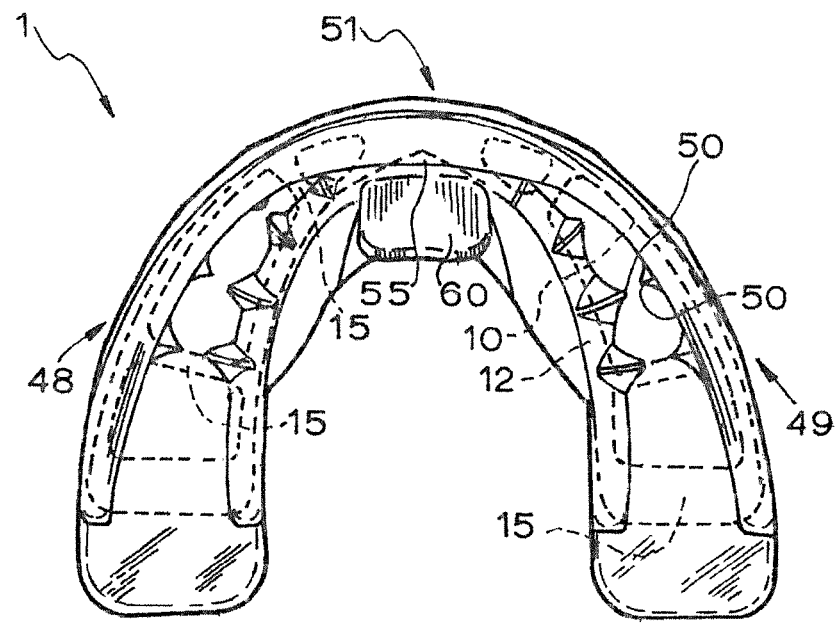
FIG. 5 is a top plan view of the appliance of FIG. 1.
Figure 6:
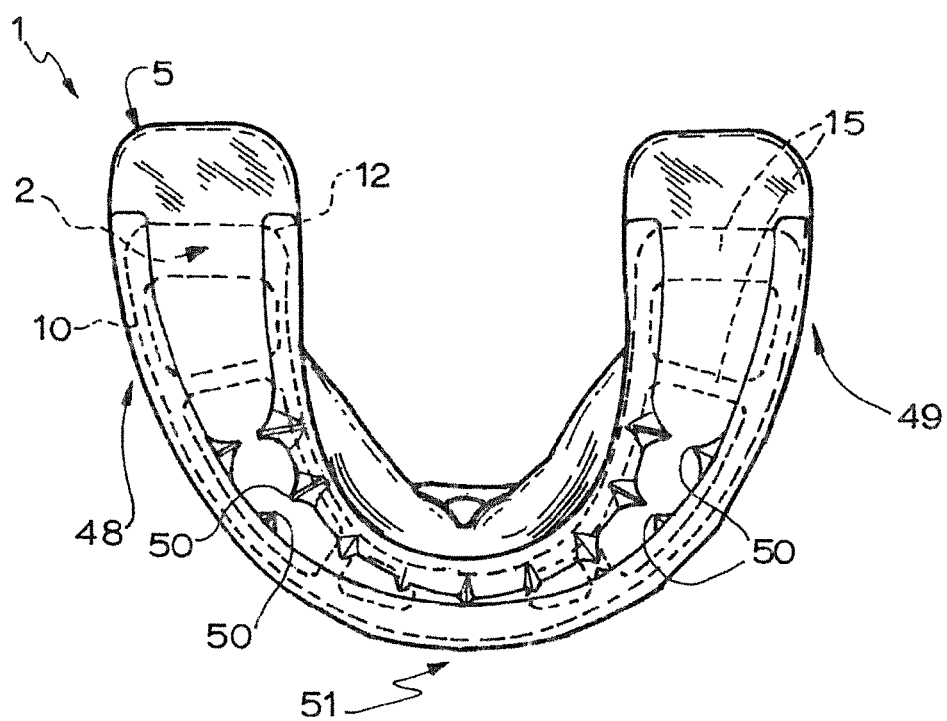
FIG. 6 is a bottom plan view of the appliance of FIG. 1.
Figure 7:
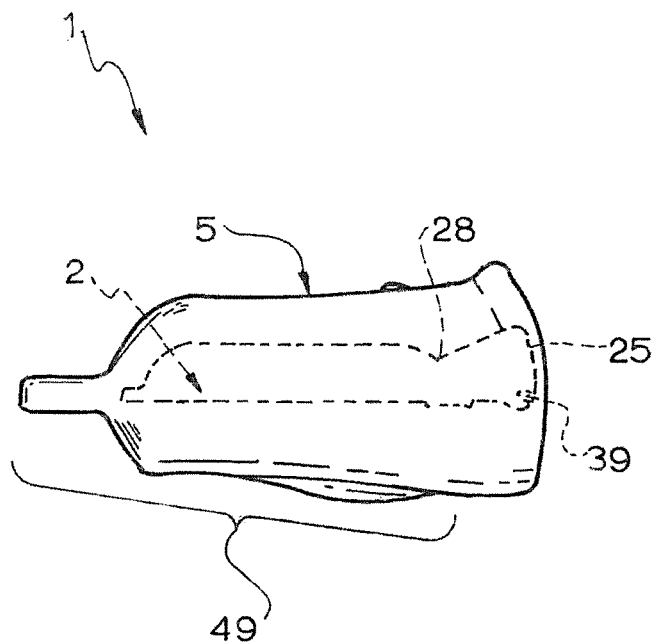
FIG. 7 is a side view of the appliance of FIG. 1 from one side.
Figure 8:
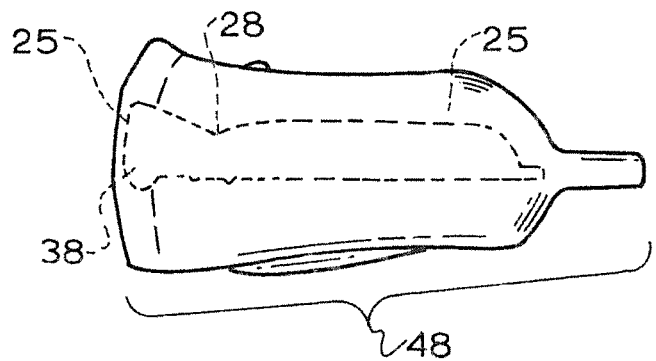
FIG. 8 is a side view of the appliance of FIG. 1 from the other side.
Figure 9:
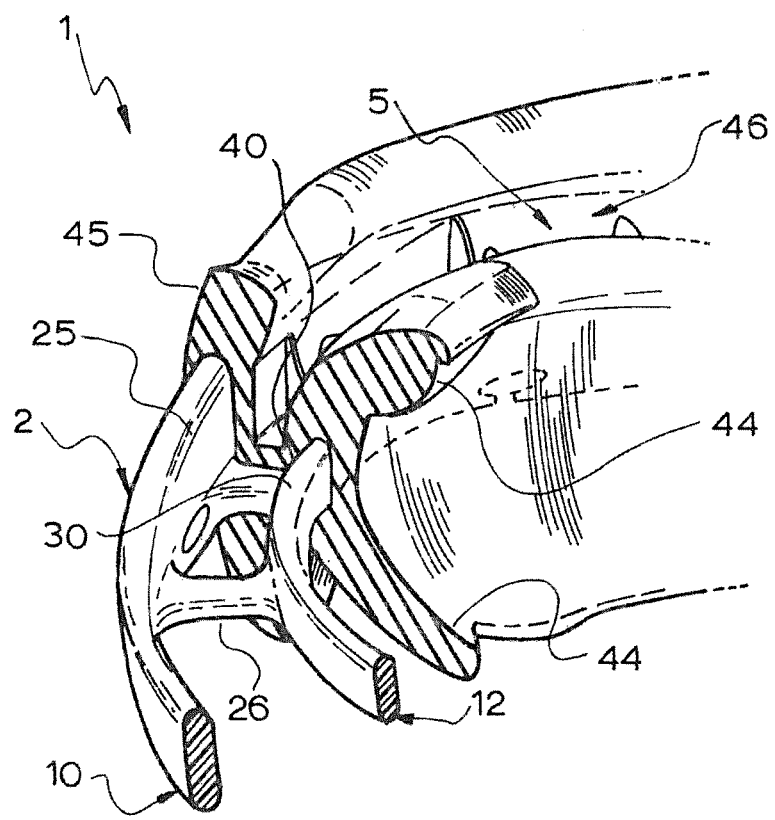
FIG. 9 is an upper three dimensional view of part of the appliance of FIG. 1 with part of a teeth engaging member thereof removed to expose an underlying base member.
Figure 19:
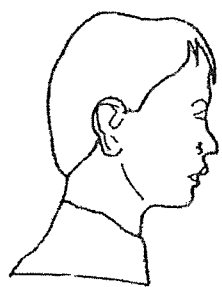
Figure 19:
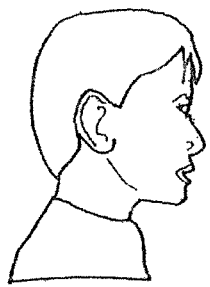
Figure 19:
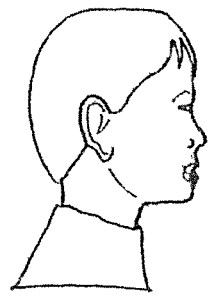
Figure 20:
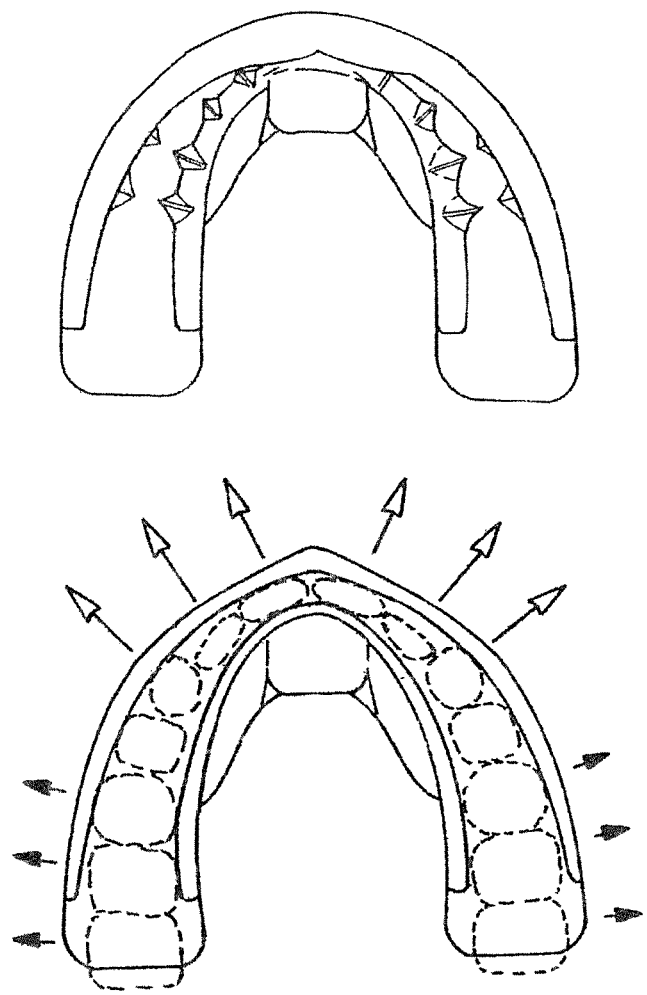
Figure 21:
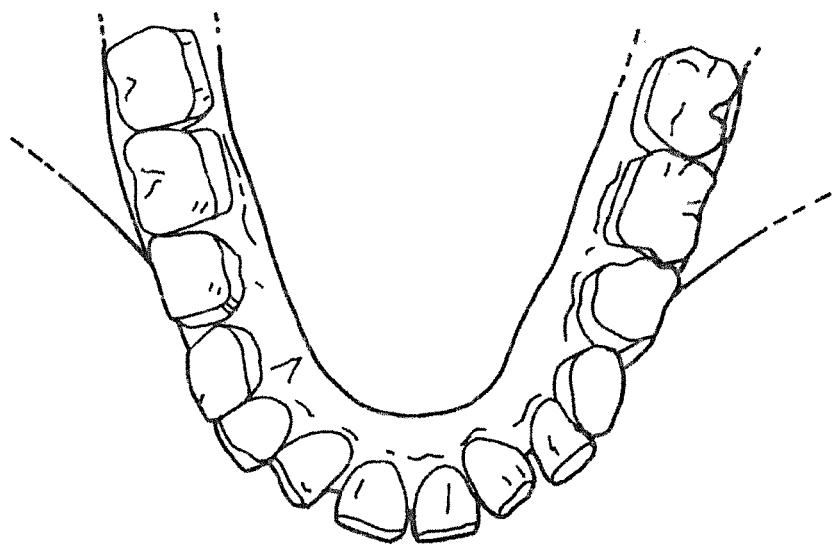
Figure 22:
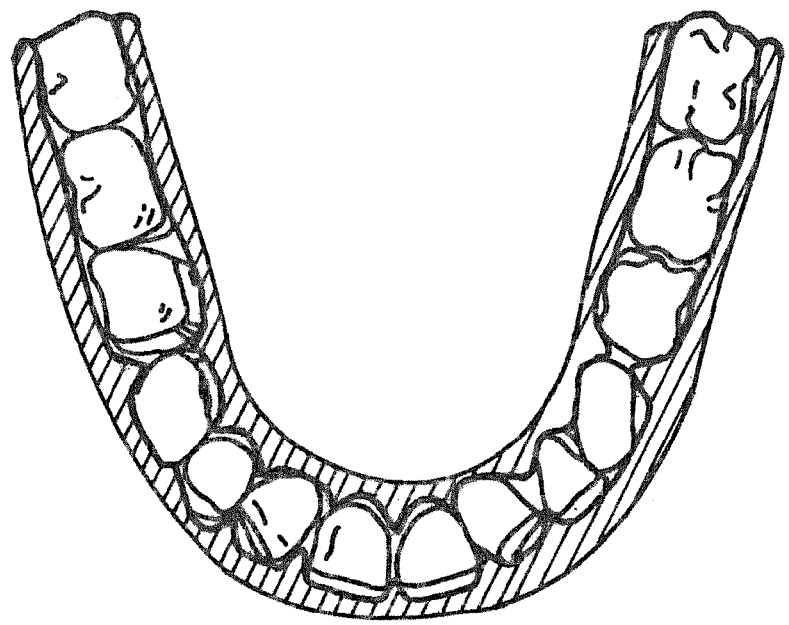
Figure 23:
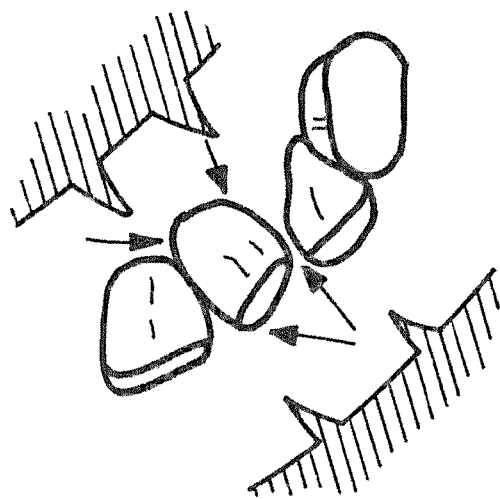
Figure 24:
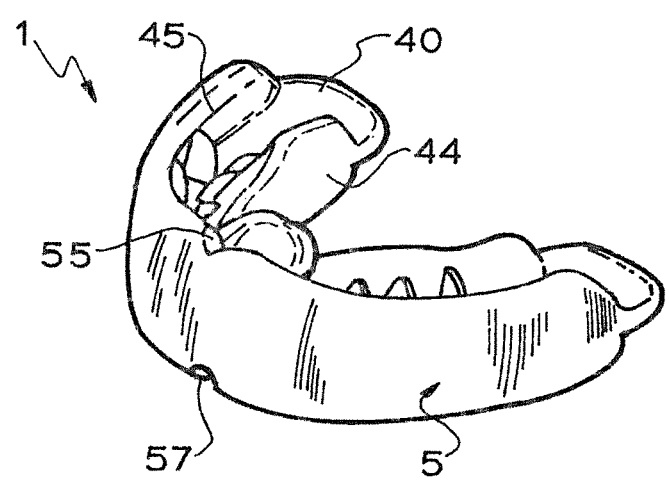

FIG. 19 shows two schematic profiles of a patient prior to treatment illustrating the effect of incorrect swallowing and mouth breathing on the profile of the patient, and a third schematic profile of a patient after treatment showing the correct positioning of the arches and lips; and FIG. 20 is a schematic drawing showing a plan view of the appliance in its resting form and also in a deformed condition which it adopts when fitted to an underdeveloped arch of a patient;

FIG. 21 is a schematic plan view of an upper arch showing the two outer incisors out of rotational alignment with the other teeth;

FIG. 22 is a schematic sectional plan view of an appliance like that in FIG. 1 mounted on the upper arch shown in FIG. 21;

FIG. 23 is an exploded schematic diagram illustrating the forces that are applied to the outer incisor in FIG. 21 to bring it into rotational alignment with the other teeth; and FIG. 24 is a perspective view of an appliance in accordance with another embodiment of the invention.

In FIGS. 1 to 9 a reference numeral 1 refers generally to an appliance that is an orthodontic appliance in accordance with the invention for promoting development of a dental arch form in a patient who has an underdeveloped arch.

The appliance 1 comprises broadly a base member 2 having a shape that corresponds generally to a dental arch form representing correct dental occlusion, i.e. a correct dental bite, and a teeth engaging member 5. The teeth engaging member 5 encloses at least part of the base member 2 and defines upper and lower dental arch receiving channels. The base member 2 is made of a resiliently flexible material, and the teeth engaging member 5 is made of a resiliently flexible material that is deformable and is softer than the resiliently flexible material of the base member 2.

The appliance 1 has a resting form in which the resilient materials of the base member 2 and the teeth engaging member 5 are in their resting condition, and the appliance 1 can be flexed or deformed out of its resting form to fit the underdeveloped dental arch form into the dental arch receiving channel. The appliance 1 when deformed in this way exerts a resting form return force that is directed to returning it to its resting form which drives expansion of the underdeveloped arch into a developed arch form.

The teeth engagement member 5 is made of silicone rubber and occupies a substantially greater volume than the base member 2 and forms the body and shape of the appliance 1. It also defines the contacting surfaces that make contact with and engage the arch and associated dental structures including the dentition and gum tissues of a patient.

Figure 10:
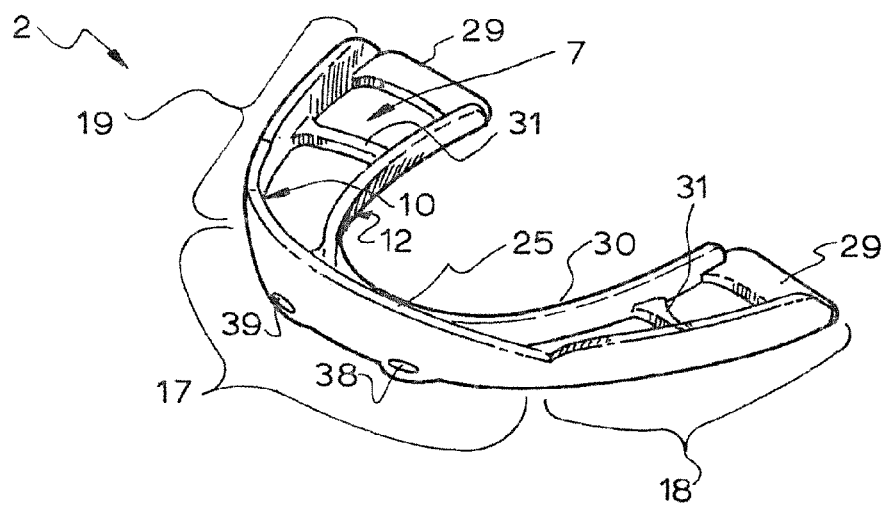
FIG. 10 is an upper three dimensional view of the base member of the appliance of FIG. 9 viewed from the front.
Figure 11:
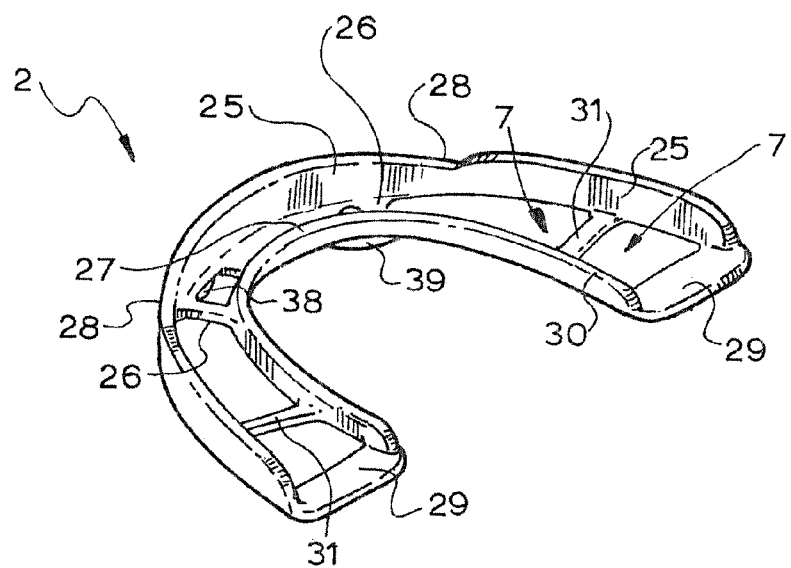
FIG. 11 is an upper three dimensional view of the base member of FIG. 10 when viewed from the rear.
Figure 12:
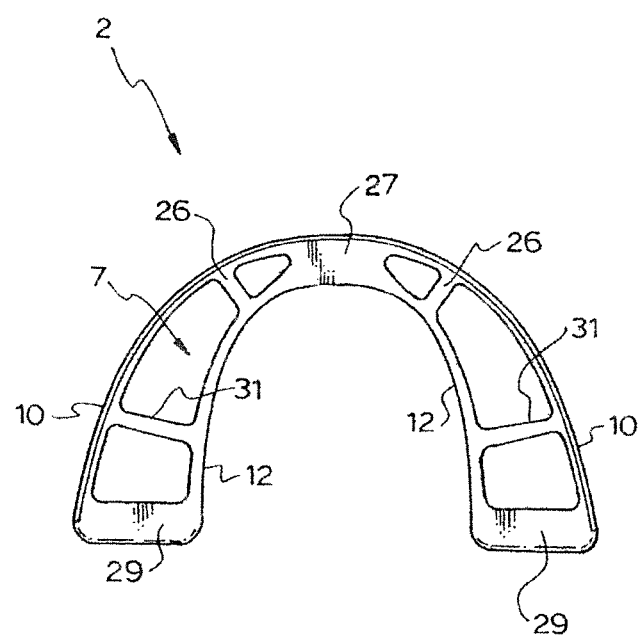
FIG. 12 is a top plan view of the base member of FIG. 10.

The base member 2 is shown in hidden detail lines in FIGS. 1 to 9 and will now be described in more detail with reference to FIGS. 10 to 12 in which it is shown separate from the teeth engaging member 5. The base member 2 comprises a front region or central frontal portion that is indicated generally by numeral 17. It also includes a left arm region 18 extending away from a left side edge of the front region 17, and a right arm region 19 that extends away from a right side edge of the front region 17. In this specification the terms left and right shall be considered from the point of view of the side of a patient's body that the feature is located on, when the appliance 1 is mounted on a dental arch of the patient. Thus the left arm region 18 will extend along the left side of a patient's arch and the right arm region 19 will extend along the right side of the patient's arch. The front region and the left and right arm regions of the base member correspond broadly to a front region and left and right arm regions of the teeth engaging member and also the appliance 1 as a whole.

The base member 2 is in the form of an open frame 7 extending in an occlusal plane comprising an arch-shaped outer longitudinal frame member 10 and an arch-shaped inner longitudinal frame member 12. The inner frame member 12 broadly follows the arch form on the outer longitudinal frame member 10 but is spaced inward of the outer longitudinal frame member 12. The open frame 7 includes a transverse frame member arrangement indicated generally by numeral 15 comprising a plurality of transverse frame members interconnecting the outer and inner longitudinal frame members 10, 12. The transverse frame members are bilaterally symmetrical on the frame and are designed to stiffen the front region 17 of the base member 2 so that it requires a greater force to be resiliently flexed than the left and right arm regions 18, 19. The front region 17 also exerts a correspondingly greater return force against the upper arch than that applied by the left and right arm regions 18, 19. Consequently when the appliance 1 is deformed to fit over a dental arch having a narrowed anterior region with protruding incisors, the appliance 1 exerts a correspondingly greater return force on the anterior region of the arch.

The transverse frame arrangement 15 includes a first pair of transverse frame members 26 including one transverse frame member towards one side edge of the front region 17 and a further transverse frame member towards the other side edge of the front region 17. The left and right transverse frame members 26 of the first pair are aligned with respectively the left and right outer incisors of a patient (i.e. the second teeth in the first and second quadrants) when the appliance 1 is fitted thereto as is shown in the drawings. The first pair of intermediate transverse frame members 26 have a width of 1-4 mm, e.g. about 2 mm.

The transverse frame member arrangement 15 also includes a front transverse frame member 27 extending between the inner and the outer longitudinal frame members 12, 10 in the front region 17 of the base member 2. The front transverse frame member 27 is positioned substantially centrally with respect to the base member 2 and extends across part of the two central incisors of a patient. The front transverse frame member 27 has a centre point midway along its length aligned with a midline of the appliance. It also has a width of about 8 to 12 mm measured from one side edge to the other and is considerably wider than the first pair of transverse frame members 26 which confers additional strength and rigidity thereon.

The first pair of transverse frame members 26 together with the front transverse frame member 27 stiffen the frame 7 in the front region of the base member 2 and a correspondingly greater force is required to deform the front region out of its resting form than is required to bend move the arm regions 18, 19. Consequently the front region applies a correspondingly greater return force to the mid-facial region of the upper arch urging it to expand. The transverse frame arrangement 15 further includes a second pair of transverse frame members 29 comprising a left and right rear transverse frame members at the rear end of the left and right arm regions 18 and 19. Each rear transverse frame members 29 has a width of 3 to 6 mm.

The transverse frame arrangement 15 further includes a third pair of transverse frame members 31 intermediate first and second pairs of transverse frame members. The third pair of intermediate transverse frame members 31 is of similar thickness to the first pair of intermediate transverse frame members 26. The third pair of intermediate transverse frame members 31 is positioned adjacent to the first premolars on the dental arch when the appliance is fitted to a patient (e.g. the fourth teeth in the first and second quadrants when viewed in plan view) and is thus positioned quite a bit closer to the rear frame members 29 than the first pair of frame members 26 on the front region 17. This predisposes the section of the base member 2 intermediate the first pair of transverse frame members 26 and the third pair of frame members 31 to form a flexure at either side of the front region when the arm regions are flexed towards each other.

The base member 2 also includes a teeth row repositioning formation that is an outer flange 25 in the form of a continuous outer wall extending along the outer frame member 10 contributing to the rigidity, including torsional rigidity, and stiffness of the base member 2. The outer flange also promotes alignment of the dentition on the upper arch.

The outer flange 25 extends across the front region 17 of the base member 2 and across left and right arm regions 18, 19 thereof. The outer flange 25 extends up to a height of 6-8 mm above the transverse frame members 15 in the front region and a height of 5-7 mm along the left and right arm regions. The height is measured from the upper surface of a proximate transverse frame member 25 to the upper edge of the inner flange 30.

The outer flange 25 also defines canine gaps 28 on the upper edge of the outer flange 25 where the eye teeth or canine teeth of a patient would be located. The upper edge of the outer flange 25 descends to a low point intermediate the central front portion 17 and the left and right portions and then ascending up again. As illustrated in the drawings the canine gaps 28 expose more of the canine teeth when the appliance 1 is being worn so that the outer flange 25 does not need to fit around the canine teeth. Applicant has observed that the canine teeth of a patient are sometimes positioned laterally outward of the other teeth prior to treatment, and the canine gaps 28 permit the canine teeth to project through the gaps and thereby enable the appliance to be fitted to a patient with considerable misalignment of the canines when that would not be the case if the canine gaps were not present.

In the illustrated embodiment the base member 2 also includes a curved inner flange 30 in the form of a continuous wall projecting up from the inner frame member 12 to a height that is 1-3 mm, e.g. about 2 mm, above the transverse frame members, which is less prominent than the outer flange 25. The height is measured from an upper surface of a proximate transverse frame member 25 to the upper edge of the inner flange 30. The inner flange 30 further contributes to the rigidity and stiffness the base member 2 and can also assist with aligning teeth in a row along the arch.

In another embodiment that has not been illustrated, the base member 2 could further include a flange depending down below either the outer frame member 10 Such a flange that also projects downwardly away from the curved outer frame member 10 further increases the strength of the base member.

In yet another embodiment of the invention that has not been illustrated the orthodontic appliance and specifically the base member thereof does not have an inner flange 30 projecting away from the inner frame member 12.

The base member 2 defines a pair of openings 38, 39 in its central front region 17 as a result of the moulding process used to manufacture the appliance 1. The openings 38, 39 are integrally formed in both the inner and outer curved frame members 12, 10 on left and right sides of the front region 17 and are aligned with corresponding openings in the teeth engaging member 5 as is shown in the drawings.

The teeth engaging member 5 that surrounds and encases the base member 2 broadly comprises a central web 40 and an inner flange 44 and an outer flange 45 (inner and outer walls 44, and 45) that project both upwardly and downwardly away from the web 40. The flanges or walls 44, 45 together with the web 40 form an upper arch receiving channel 46 and a lower arch receiving channel 47 within which the upper and lower dental arches and associated dentition of a patient are received. The web 40 forms occlusal bite surfaces with the channels against which the bite surfaces of the dentition of the upper and lower dental arches bears.

The teeth engaging member 5 comprises a front region 51, and left and right arm regions 48 and 49 corresponding to the front region 17 and left and right arm regions 18 and 19 of the base member 2. The front region 51 of the teeth engaging member 5 is mounted over and encloses the front region 17 of the base member 2 and has the same extent as the front region 17 of the base member 2. That is the length of the front regions 17, 51 of respectively the base member 2 and the teeth engaging member 5 broadly coincide. The left and right arm regions 48, 49 have a greater longitudinal extent than the left and right arm regions of the base member 2 as shown in the drawings and particularly in FIGS. 2, 5 and 6. That is the rear edges of the teeth engaging member 5 are spaced rearward of the rear edges of the base member 2. The teeth engaging member 5 fills in the space between the inner and outer longitudinal frame members 12, 10 and the transverse frame members 26, 27, 29 and 31 also forms a layer having some thickness above and below the inner and outer frame members 12, 10.

The appliance includes a plurality of complementary pairs of teeth positioning formations on the teeth engaging member projecting into the upper and lower arch receiving channels which are indicated generally by the reference numeral 50. This in turn is divided up into pairs of upper arch teeth positioning formations that project into the upper arch receiving channel and pairs of lower arch teeth positioning formations that project into the lower arch receiving channel. Both the complementary pairs of teeth positioning formations on the upper and lower arches are arranged in a bilaterally symmetrical fashion on the appliance.

Each complementary pair of upper arch teeth positioning formations comprises an outer teeth positioning formation projecting into the upper arch receiving channel from the outer wall and an inner teeth positioning formation projecting into the upper arch receiving channel from the inner wall. Further each complementary pair of upper arch teeth positioning formations is located at a predetermined position along the arch form so as to project into a space between two specific adjacent teeth. The outer and inner teeth positioning formations of each complementary pair are aligned with each other in a direction transverse to the line of the arch form.

Each upper and lower arch teeth positioning formation comprises a wedge formation that is substantially vertically extending. Further each wedge formation includes a wedge base on the inner or outer wall and a wedge apex that projects away from the wedge base into the upper arch receiving channel. Further each wedge formation is integrally formed with the associated inner or outer wall of the teeth engaging member of a resiliently deformable material and is made of the same material as the wall.

The upper arch teeth positioning formations include two pairs of complementary teeth positioning formations positioned on either side of a midline of the appliance for projecting into an interproximal space between the inner and outer incisors on the left and right sides. Two further pairs of complementary teeth positioning formations are positioned for projecting into an interproximal space between the outer incisors and the canines on the left and right sides. Two further pairs of complementary teeth positioning formations are positioned for projecting into an interproximal space between the canines and the pre-molars on the left and right sides. Two further pairs of complementary teeth positioning formations are positioned for projecting into an interproximal space between the pre-molars and the adjacent molars on the left and right sides. One further pair of complementary teeth positioning formations is positioned on the midline of the appliance for projecting into an interproximal space between the left and right inner incisors on the patient. The complementary pairs of adjacent teeth positioning formations assist in promoting expansion of the arch form. They also assist in positioning the different teeth along the arch form in their correct positions along the arch. Further they also assist in the rotational realignment of teeth that are out of alignment on the arch.

Thus each pair of teeth positioning formations comprises an outer positioning formation on the outer wall 45 of the member 5 projecting into the dental arch channel, and an inner teeth positioning formation on the inner wall 44 projecting into the dental arch channel. The inner and outer formations in each pair are aligned with each other in a direction that is transverse to the length of the channel.

Each teeth positioning formation is wedge shaped when the appliance is viewed in plan view. It tapers inwardly from both sides on the wedge base to the wedge apex where it forms a sharp point of the wedge. The wedge apex extends in a straight line broadly perpendicularly away from the plane of the web as shown in the drawings. That is the wedge apex is broadly vertically extending when the appliance is fitted to a patient and is designed for projecting into the interproximal space between two adjacent teeth on a patient's arch in use.

In the illustrated embodiment there are nine pairs of adjacent teeth positioning formations on the upper channel for interacting with the upper dental arch structures of a patient. The teeth engaging member 5 includes a corresponding arrangement of complementary pairs of lower arch teeth positioning formations projecting into the lower arch receiving channel for acting in the same way on the lower dental arch and associated dental arch structures of a patient.

The complementary pairs of adjacent teeth positioning formations are positioned so that each formation is located between two adjacent teeth on the dental arch. The wedge shape of the teeth positioning formations tends to urge teeth apart from each other and form a space between adjacent teeth. The adjacent teeth positioning formations are in particular located towards the anterior region of the arch and thus promote arch expansion in this way in the anterior region of the arch. As the teeth on the dental arch are generally in end to end contact when the treatment commences, the only way that additional space can be created to form the spaces between adjacent teeth is for the arch to expand. That is the wedge formations project into the space between adjacent teeth and push them apart which in turn urges the arch to expand to create additional arch length.

The wedge formations are positioned in pre-determined positions along the arch line corresponding to desired positions of individual teeth and during treatment the taper of the wedges guide the individual teeth towards these positions. Thus the teeth positioning formations also help to position individual teeth on the dental arch.

The orthodontic appliance 1 includes a notch or cut-out 55 in the midline of the upper surface of the outer flange 45 and a smaller midline notch or cut-out 57 in the lower surface of the outer flange 45. The notches 55, 57 form a recess or gap on the appliance midline so that the member 5 does not come into contact with soft tissue in the area of the dental midline. The orthodontic appliance 1 also has a tongue tab 60 formed on the inner flange 44 above the web 40 (with gaps on either side thereof) for training a patient to correctly position their tongue to improve their oral habits and particular to avoid tongue thrusting. The inner flange also defines a small notch 57 on the lower edge of the inner flange. The spaces and notches help to facilitate inward and outward flexing of the arm regions 48, 49 of the teeth engaging member 5 of the appliance 1 when it is fitted to an underdeveloped arch.

Further the occlusal surfaces of the web 40 of the teeth engaging member 5, e.g. upper and lower faces thereof, taper outwardly from the front region 51 of the member 5 in a rear direction to the left and right trailing arm regions 48, 49 to progressively thicken the web 40 up to a point of maximum thickness spaced forward of the rear ends of the arm regions. Thereafter the upper each other so as to progressively thin the web from said point of maximum thickness to the rear of the teeth engaging member 5. The teeth engaging member 5 also has open passages therein corresponding to the apertures 38, 39 of the base member 2.

In use the orthodontic appliance 1 described above will typically be initially fitted by an orthodontist or a dentist.

A first step in fitting an appliance 1 is to choose an appropriately sized appliance from the different sizes of appliances. The range of appliances 1 envisaged by the Applicant will have at least three different sizes of base member defining the basic arch form. Each of these base member sizes will then have at least four different sizes of teeth engaging member with different arrangements of complementary pairs of teeth positioning formations thereon. Generally an orthodontist will choose a size of appliance after inspecting and measuring the dental arch and associated dental arch structures of the patient using a suitable measuring device that is supplied to the dental practitioner. They will also look at the position of the teeth along the arch form.

Figure 13:
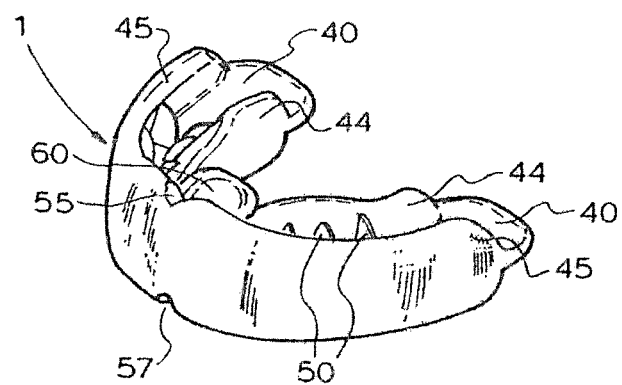
FIG. 13 is a three dimensional view of the appliance of FIG. 1 in its resting or original condition prior to use.
Figure 14:
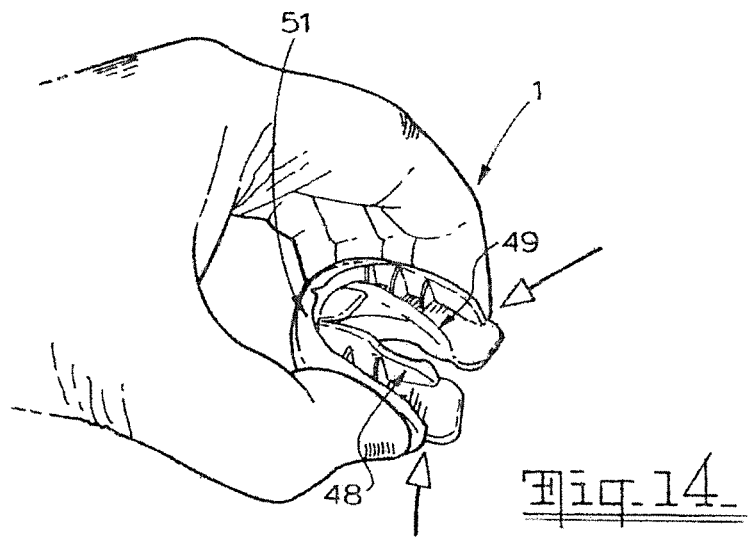
FIG. 14 is a schematic three dimensional view of the appliance of FIG. 13 showing how left and right arm regions can be moved towards each other by hand pressure being applied by a patient or a dental practitioner.
Figure 15:
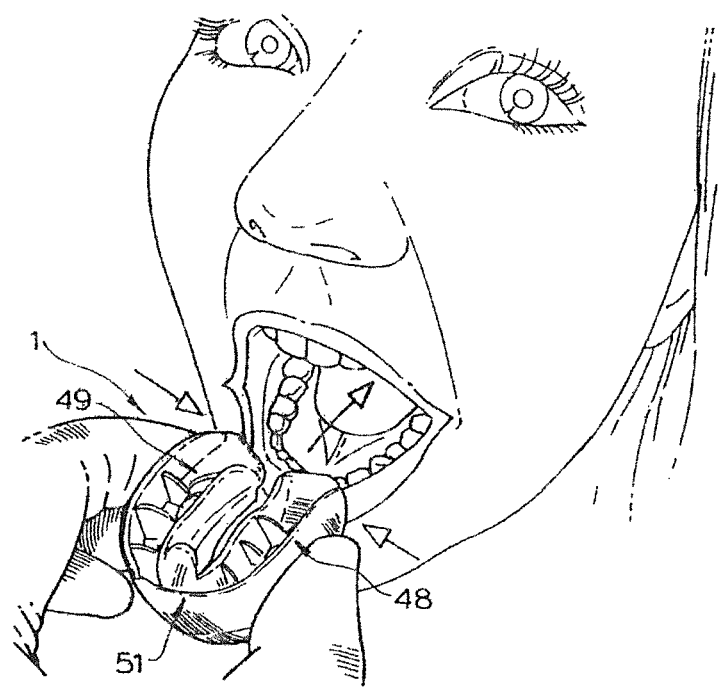
FIG. 15 is a schematic three dimensional view of the appliance of FIG. 13 showing a dental practitioner fitting the appliance to a patient having an underdeveloped arch with the dentist squeezing the left and right arm regions towards each other to fit the appliance over the underdeveloped dental arch of the patient.
Figure 17:
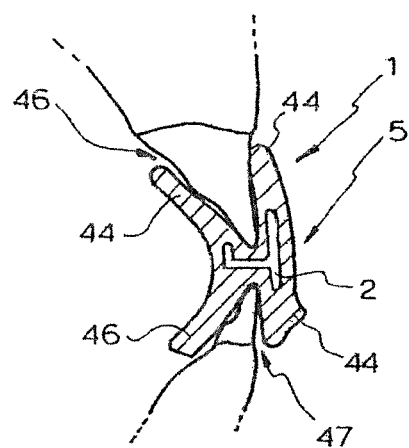
FIG. 17 is a schematic sectional side view of the appliance fitted to the upper arch of a patient along a dental midline.

This procedure of fitting the appliance to a patient's dental arch is shown schematically in FIGS. 13 to 15. Where the patient has an under developed arch structure such as that found in a class 2 malocclusion, the dentist will manually flex the appliance to an extent that enables it to be fitted onto the patient's dental arch so that the arches are received within the respective arch receiving channels with a tight fit and a tight grip as shown schematically in FIG. 17. This flexing may involve deformation of the arm regions as well as the front region which is stiffer than the arm regions. The arches are received within the respective arch receiving channels with a tight fit as shown schematically in FIG. 17. The inner and outer walls (flanges) 44 and 45, and the occlusal surfaces of the web 40 of the teeth engaging member 5, bear against the upper and lower dental arches and the associated arch structures such as the teeth. In addition the wedge formations of the pairs of teeth positioning formations also bear against the teeth that are adjacent to them.

The soft silicone rubber of the teeth engaging member 5 is in contact with and bears against the dental structures including the gums and teeth of the patient. The silicon rubber cushions the underlying force being applied by the deformed base member so that the appliance is reasonably comfortable to wear despite the resting force return force that is being applied to the arch to encourage expansion of the arch.

The appliance is an active appliance. As such the appliance and particularly the base member 2 thereof generates a force that bears against the dental arch and associated dental structures of the patient that have a physiological influence on the bone development of the dental arch form that drives expansion of the arch form. The dental arch forms are encouraged to develop into an arch form corresponding to the respective arch receiving channels within which they are received which correspond to a developed arch form that is conducive to correct dental occlusion. The resting form return force generated by the appliance when fitted to an underdeveloped arch form is analogous to active spring energy.

Figure 16:
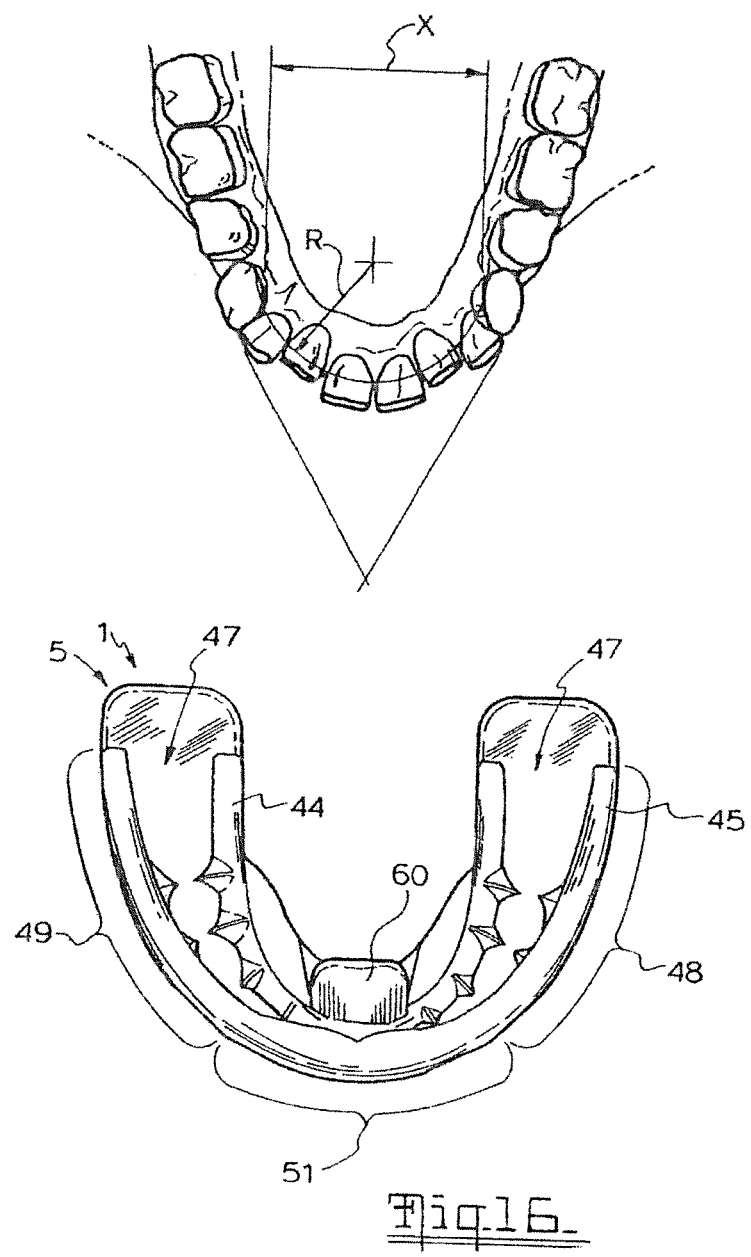
FIG. 16 is a schematic top plan view of the appliance of FIG. 13 in a resting state positioned next to a dental arch of a patient having an underdeveloped arch that is typical of a class 2 malocclusion.

FIG. 16 shows an appliance in its original shape next to an underdeveloped dental arch that requires expansion into a more developed arch form. The drawings clearly show how the arch form of the appliance 1 is noticeably wider than the underdeveloped dental arch form of the patient. Consequently the appliance 1 has to undergo significant deformation to fit the appliance 1 over the underdeveloped arch form of the patient. The deformation causes the appliance 1 to exert a buccally directed return force against the dental arch and associated dental structures of the patient, particularly in the narrowed anterior region thereof.

Figure 18:
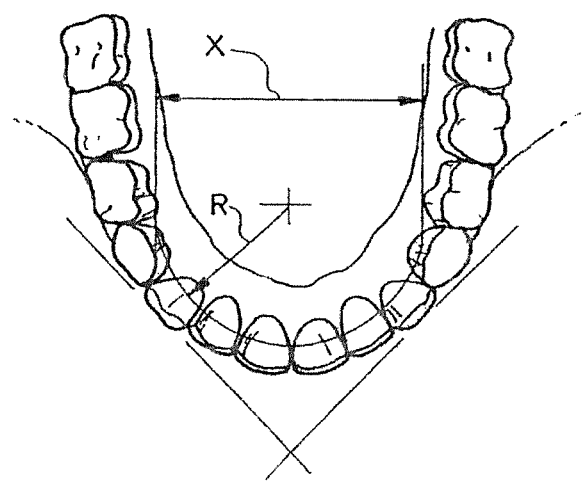
FIG. 18 shows the arch shown in FIG. 16 after the orthodontic treatment of the patient has progressed to the point where the patient's arch has undergone some development.

Over time this force progressively develops the arch form to become more and more like the arch form defined by the resting form of the appliance. FIG. 18 shows the arch of the patient of FIG. 15 after it has undergone treatment with the oral appliance and the anterior region of the arch has widened into a developed arch form. The distance "X" between the inner surface of the left and right canine teeth in FIG. 18 is much greater than the corresponding distance of the dental arch in FIG. 16. Further the radius of curvature of the line of teeth in the anterior portion of the arch in FIG. 18 shown by "R" is much greater than the corresponding radius of the dental arch in FIG. 18. This shows how the arch and in particular the anterior region thereof is developed.

The complementary pairs of upper arch teeth positioning formations 50 assist in driving expansion of the upper arch of the patient. The complementary pairs of upper arch teeth positioning formations insert into the interproximal spaces between adjacent teeth. This moves the teeth apart from each other which requires an increase in the length of the arch and for this to occur the arch has to expand. Thus the complementary pairs of upper arch teeth positioning formations drive arch expansion.

The creation of space between adjacent teeth on the arch line is also important because it frees the teeth up to move into their correct position under the influence of the appliance. In situations where a treatment appliance does not provide any space between adjacent teeth, the f movement of the teeth may be hindered by another tooth. For example in cases where the teeth are very close to each other one tooth may be wedged behind an adjacent tooth which blocks its movement to expand the arch and move into alignment with the adjacent teeth. The creation of space between adjacent teeth with the complementary pairs of upper arch teeth positioning formations solves this problem. After the treatment has been completed the gaps between the adjacent teeth close up naturally. Further the appliance 1 does this along substantially the entire arch simultaneously and this frees a line of teeth so that they can move independently under influence of the appliance. Applicant has found that prior art orthodontic bands that are placed over a tooth for this purpose exert a very local effect only on specific teeth and this may have the effect of crowding the next adjacent teeth along the arch.

In addition to influencing arch development on the patient the orthodontic appliance 1 and particularly the walls of the teeth engaging member 5 are in contact with the dentition and apply an aligning force to the dentition. The application of force to move teeth is standard practice in orthodontics and the physiological mechanism by which tooth movement is accomplished is understood by the dental and orthodontic community and will not be described in this specification.

The inner and outer walls defining the channels are particularly influential in aligning the dentition along the curve of the channel. The rigidity of the base member 2, and in particular the continuous inner and outer flanges on the base member 2, contribute to the teeth aligning force that is generated by the inner and outer walls. It encourages protruded and retruded teeth that are out of alignment with the other teeth to move into alignment with other teeth in the arch form. The complementary pairs of teeth positioning formations bear against the surfaces of the dentition and also contribute to alignment of the teeth along the arch.

The appliance 1 also operates to rotate misaligned teeth back into rotational alignment with the remainder of the teeth such as those on the upper arch illustrated in FIG. 21. As shown in FIG. 22 it does this by virtue of the deformation of the inner and outer walls which bear against the teeth and also deformation of the pairs of teeth positioning formations. The deformed walls and teeth positioning formations apply a force to the tooth that tends to rotate the tooth back into a position defined by the resting form of the appliance. The pairs of teeth positioning formations are particularly important to achieving this rotational realignment. Applicant has found that the outer incisors are often rotated out of alignment on a patient. The mesial edge of the tooth is rotated bucally and the distal edge is rotated palatally, and the appliance 1 is very efficacious at rotating them back into alignment as is illustrated schematically in FIG. 23.

The orthodontic appliance is a removable appliance that is worn for a number of hours each day, e.g. for a few hours during the day and at night while the patient is sleeping, and is not worn by a patient at other times of the day. As the appliance has both upper and lower channels that receive both the upper and lower dental arches of a patient, it is not suitable for being worn while the patient is carrying out certain activities. For example a patient would not be able to talk or eat while they were wearing the appliance. Over time with proper use of the appliance and good patient compliance, the application of force by the base member that has been deformed out of its original shape will cause the arch to develop and the crowding of teeth on the arch to diminish. With further treatment the teeth will move towards aligning with each other along the arch form.

FIG. 19 shows a sequence of schematic profiles of a patient showing how their profile develops with the progression of treatment with the orthodontic appliance. The first two drawings show the effect of incorrect swallowing and mouth breathing on the profile of the patient. This is evident in the relative positioning of the upper and lower arches and the lip profile. The third drawing shows the profile of the patient after treatment has been completed. The upper and lower arches are correctly positioned relative to each other in the third drawing and the lips are together.

FIG. 20 is a basic schematic drawing showing a plan view of an appliance that is similar but not necessarily the same as that of FIG. 1 in a resting condition and also shows how the appliance can be deformed to fit it to an underdeveloped dental arch of a patient. In the schematic drawing the patient has an underdeveloped upper arch that needs to be expanded, particularly in the anterior region thereof. The front region of the appliance in particular is flexed and deformed to fit the appliance to the arch. The front region has a greater stiffness than the left and right arm regions of the appliance as has been described above. Consequently when deformed, the front region exerts a return force that is related to the force required to flex it out of its resting condition and this return force is applied to the underdeveloped arch of a user to encourage it to develop. This force is greater than the force applied by the arm regions when they undergo a corresponding amount of deformation or flexing. The arrows on the schematic drawing indicate schematically the direction and the strength of the return force that is applied by the deformed front region of the appliance. The longer arrows in the front region shown in the drawings show that the return force applied by the deformed front region is greater than the return force applied by the arm regions when flexed. The strong return force applied by the front region of the appliance encourages the anterior region of the dental arch corresponding to the incisors and the canines to develop. It is to be understood that this schematic drawing is provided purely to assist an addressee with an understanding of the disclosure and is not to be regarded as a detailed drawing that is dimensionally exact.

The manufacture of the appliance by a moulding operation will now be described. During manufacture of the orthodontic appliance the base member 2 is injection moulded in a first injection moulding step, and the teeth engaging member 5 is then moulded around the base member 2 in a second moulding step.

In one form a co-injection moulding process is used in which the base member 2 is moulded in a first step by an injection moulding process and then the teeth engaging member 5 is moulded directly onto the base member 2 in a second moulding step without it being removed from the mould. The base member 2 does not have to be removed from the mould for the teeth engaging member 5 to be moulded onto it. The mould comprises two mould parts, a first mould part for the base member 2 and a second mould part for the teeth engaging member 5.

The base member 2 is made of a polymeric material having suitable physical properties of stiffness and resilient flexibility to enable the appliance to perform its orthodontic function. In the illustrated embodiment the base member is made of a polyamide material that is nylon. Nylon is a generic name of any long chain synthetic polymeric amide which has recurring amide groups as an integral part of the main polymer chain. The polymer is linear and as such is suited to being formed into a filament although it can also be used to form a three dimensional body. Nylon has been found to have an appropriate level of rigidity yet the base member as a whole is resiliently flexible and can be resiliently flexed out of its resting form so that the left and right arm regions of the base member can be moved towards and away from each other. It also permits some twisting of the left and right arm regions relative to each other. Further Nylon has a high melting temperature so that when a material having a high injection temperature, e.g. silicon rubber is used as the material for the teeth engaging member can withstand the injection temperature of silicone when it is injected onto the base member to form the teeth engaging member.

Applicant has obtained Nylon from Shinko Chemical Company based in Taipei, Taiwan. The table below indicates the different grades of Nylon 66 supplied by this company.

| | | | | | | | |
|---|---|---|---|---|---|---|---|
| TENSILE STRENGTH | Kg/cm² | 800 | 900 | 1700 | 1900 | 840 | 1150 |
| ELONGATION | % | 55 | 10 | 7.1 | 2 | 4 | 4.5 |
| FLEXURAL STRENGTH | Kg/cm² | 1000 | 1350 | 2300 | 2600 | 1200 | 1700 |
| FLEXURAL MODULUS | Kg/cm² | 28000 | 35000 | 80000 | 108000 | 31000 | 72000 |
| IZOD IMPACT STRENGTH | Kg-cm/cm | 13 | 8.5 | 11 | 9 | 7.3 | 7 |
| ROCKWELL HARDNESS | R-SCALE | 118 | 119 | 120 | 120 | 118 | 119 |
| MELTING POINT | °C. | 260 | 260 | 255 | 260 | 260 | 260 |
| M.D.T (18.6kG/cm2) | °C. | 66 | 200 | 238 | 240 | 73 | 248 |
| M.D.T (4.6kG/cm2) | °C. | 230 | 240 | 255 | 255 | 230 | 245 |
| ASH CONTENT | W1% | | 13 | 33 | 45 | — | 25 |
| MOLD SHRINKAGE | | 1.7-1.8 / 1.3-1.4 | 0.3-0.5 / 0.8-1.0 | 0.2-0.4 / 0.7-1.0 | 0.2-0.3 / 0.3-0.5 | 1.0-1.3 / 0.7-1.0 | 0.3-0.5 / 0.7-1.0 |
| M.F. | g/10 min | 55 | 20 | 13 | 10 | 43 | 20 |
| SP Gr | g/cm² | 1.1 | 1.2 | 1.35 | 1.46 | 1.16 | 1.38 |

A grade of Nylon can be used having a tensile strength 800-1000, e.g. about 900, a flexural Strength 1000-1500, e.g. about 1350, and a ROCKWELL Hardness of 90-150, e.g. about 119. In particular Applicant has used a grade of nylon known as Nylon 66 6212GA for the manufacture of appliances in accordance with this invention.

In the illustrated embodiment the teeth engaging member is formed of a silicone rubber. A medical grade silicon rubber is a basic commodity that can be obtained from a number of suppliers such Du Pont Chemical Company based in Delaware in the USA. Applicant has sourced a suitable silicone rubber from a Japanese chemical company by the name of Shin-Etsu Chemical Co Ltd based in Tokyo, Japan. The material specification data sheet provided by Shin-Etsu for this material is provided below.

| SHIN-ETSU ®TWO-COMPONENT SILICONS RUBBER COMPOUND | | | | |
|---|---|---|---|---|
| | | Transparent High Strength | | |
| Typical Properties | Units | KE-1950-50 (A-B) | KE-1950-60 (A-B) | KE-1950-70 (A-B) |
| Viscosity in mPa·s (P) Brookfield-type rotational viscometer | | 680 (6800) | 730 (7300) | 750 (7500) |
| Specific Gravity at 25° C. (77° F.) | g/cm³ | 1.13 | 1.14 | 1.15 |
| Mixing Ratio A:B | | 1:1 | 1:1 | 1:1 |
| Hardness | JIS-A | 50 | 58 | 68 |
| Tensile Strength | JIS-6301 | Mpa 9.3 | 7.8 | 7.8 |
| Elongation at break | JIS-6301 | % 55 | 380 | 350 |
| Tear Strength | JIS-6301 | kN/m 44.1 | 43.1 | 49 |
| Compression set | 22 h/150° C. | (%) 28 | 22 | 50 |
| Linear Shrinkage | JIS-6301 | (%) 2 | 1.9 | 2.1 |
| Volume Resistivity Comments Ω-m | | 10 T | 10 T | 10 T |

Applicant uses the KE-1950-70 grade of silicon supplied by Shin-Etsu, which is the hardest grade and which has the following properties:

Hardness of 50-68 according to JIS-A;

Tensile strength of 7.8 to 9.3 MPa according to MS-6301;

Elongation at break 55 to 350% according to JIS-6301; and

Tear strength of 43.1 to 49 KN/m according to JIS-6301.

In the first moulding step the first mould part is mounted in an operative moulding position in a moulding zone and molten nylon is injected into the first mould part to form the base member 2. Thereafter the first moulding part is withdrawn from the moulding zone and the second moulding part is moved into its operative position in the moulding zone. Molten silicon rubber is injected into the second mould part in the second moulding step to mould the teeth engaging member onto the already moulded base member. The second moulding part is then withdrawn to reveal the newly moulded appliance which can be removed from the die once the moulded silicon rubber material has had an opportunity to cool sufficiently for it to be handled. The cycle times for each of the moulding steps is typically about 15 seconds. The cycle time for the silicone rubber moulding is longer than that for the nylon base member. Generally the moulded pieces are allowed to cool passively. However the silicone rubber can be actively cooled once it has been moulded. Nylon is capable of withstanding the injection temperature of silicone and this property as well as its other physical properties that make it suitable for use in the base member of the appliance.

In another form the appliance 1 can be moulded in two separate dies with the base member being moulded in a first die then the base member can be removed and be placed in a second die where the teeth engaging member is moulded onto the base member 1.

In another example embodiment of the invention the base member 2 is made out of nylon and the teeth engaging member is made of polyvinylchloride (PVC). PVC resin is a staple commodity that is supplied by a number of chemical manufacturers including IMPRODEX which is a division of Pacific Dunlop Limited based at 135 Racecourse Road, Flemington, VIC, Australia. Applicant used the HYCO 4016-89 PVC which is a clear extrusion grade PVC supplied by IMPRODEX.

An appliance in which PVC is substituted for silicon is manufactured by a similar two step moulding process to that described above. The base member is moulded of nylon in a first step and then the teeth engaging member is moulded of PVC in a second moulding step. An advantage of using PVC instead of silicone rubber is that it does not require as high an injection temperature as silicon rubber and this reduces the mould temperature that the mould equipment and the material of the base member must be able to withstand when the molten PVC is injected into the mould. This opens up the possibility of using other materials for the base member including addition polymers, such as polyethylene, and polypropylene, condensation polymers such as polyurethane and polycarbonate, and thermoplastic elastomers such as santoprene.

In use an orthodontic appliance with a member 5 made of PVC is used in the same way as the appliance described above and functions in exactly the same way when fitted to the dental arch and associated arch structures of the patient.

FIG. 23 illustrates an orthodontic appliance in accordance with another embodiment of the invention. In this embodiment the appliance comprises a teeth engaging member on its own and does not have an internal base member received therein. Unless otherwise indicated the same reference numberals will be used to refer to the same components as in the embodiments above.

The teeth engaging member and the complementary pairs of teeth positioning formations formed thereon are integrally moulded from a single resiliently flexible material. In the illustrated embodiment a medical grade of silicon rubber is used. This embodiment does not have the level of stiffness that is exhibited by the FIG. 1 embodiment and therefore does not exert the same level of return force when it is deformed. However otherwise it functions much like the first embodiment. In particular the complementary pairs of teeth positioning formations 50 assist in urging adjacent teeth along the arch line to move apart from each other and thereby expand the arch form.

An advantage of the appliance described above with reference to the drawings is that it is an active appliance that directs a force with sufficient strength onto the dental arch of a patient to develop the arch form within a reasonable treatment time. In particular it can apply a force (spring energy) that is comparable to that applied by orthodontic braces and is capable of developing an underdeveloped arch to develop into a more fully developed arch form with improved dental occlusion. In addition to promoting arch expansion due to the resilience of the appliance, the appliance also has complementary pairs of teeth positioning formations that further promote expansion of the arch form (i.e. in addition to the spring energy of the appliance). The teeth positioning formations are forced into the interproximal spaces between adjacent teeth and the only way to achieve this is to increase the length of the arch line and expand the arch.

A further advantage of the appliance described above is that it assists in aligning the dentition on the upper and lower dental arches. The inner and outer walls of the teeth engaging member bear against the surfaces of the teeth and promote an alignment of the teeth along the arch line represented by the resting form of the appliance. The pairs of teeth positioning formations also assist with teeth alignment. In some embodiments the flange or continuous wall on the outer curved frame member of the base member stiffens the outer wall so that it applies a stronger aligning force to the teeth.

A yet further advantage of the appliance is that is can successfully rotate mis-aligned teeth back into alignment. If one or more teeth are rotated, with the distal edge being protruded and the mesial edge being retruded, then the consequent deformation of the inner and outer flanges defining the respective arch receiving channel applies a rotational force to the rotated teeth. This encourages rotational realignment of the rotated teeth into a non-rotated position. The complementary pairs of teeth positioning formations also assist with rotational realignment of individual teeth that have been rotated by providing additional surfaces which apply a rotating force to the teeth to move them back into alignment. As it is common for teeth to be rotationally misaligned, in particular the outer incisors or second teeth, it is particularly advantageous that the appliance can correct this problem.

A further advantage of the orthodontic appliance described above is that the silicone rubber is a soft material that has an ability to deform significantly to fit the appliance to the dental arch structure of a patient having a shape that is quite different to that of the appliance. It also bears against the dental arch and dental structures of the patient and cushions the appliance against the dental arch and arch structures. As a result the teeth engaging member does not apply excessive local pressure to the teeth and gums, and is comfortable to wear even when the base member has been significantly deformed. This is important because a patient has to be able to sleep and perform other activities while they wear the appliance and patient comfort is an important factor in obtaining patient compliance which is the key to successful treatment outcomes. Further unlike orthodontic braces the appliance does not have sharp surfaces that can injure the intro-oral soft tissues.

A yet further advantage of the orthodontic appliance described above is that it is pre-formed or manufactured in a number of sizes in a moulding operation and these sizes can then be fitted to a significant cross-section of the population. Thus the appliance can be manufactured in a commercial scale manufacturing operation in large quantities and is not custom made for each patient. In particular the appliance can be injection moulded and supplied to the market at a lower cost than existing orthodontic treatments including braces. This opens up the possibility of orthodontic treatment becoming accessible to a broader cross section of the population.

It will of course be realised that the above has been given only by way of illustrative example of the invention and that all such modifications and variations thereto as would be apparent to persons skilled in the art are deemed to fall within the broad scope and ambit of the invention as herein set forth.

The invention claimed is:

1. An orthodontic appliance for developing a dental arch form and alignment of the teeth of a patient, the orthodontic appliance comprising:
  a resiliently deformable teeth engaging member that includes an arch-shaped web that defines upper and lower occlusal bite surfaces, the teeth engaging member has inner and outer walls that project transversely away from the upper surface of the web, and the web and the inner and outer walls define an upper arch receiving channel within which an upper dental arch and associated dentition of the patient can be received;

at least one complementary pair of upper arch teeth positioning formations on the teeth engaging member for expanding the arch and positioning individual teeth along the upper arch, each said complementary pair comprising an outer teeth positioning formation projecting into the upper arch receiving channel from the outer wall and an inner teeth positioning formation projecting into the upper arch receiving channel from the inner wall, the upper arch teeth positioning formations each being resiliently deformable and comprising a wedge formation including a wedge base on the inner or outer wall and substantially planar wedge faces projecting away from the wedge base to a wedge apex adapted to project into an interproximal space between two adjacent teeth of the patient when the orthodontic appliance is fitted to the patient; and an arch-shaped base member including a frame extending in a plane parallel to the web that is received within and is substantially enclosed by the teeth engaging member, the base member being formed of a resiliently deformable material having a greater rigidity than the teeth engaging member, wherein the orthodontic appliance has a resting form and can be deformed out of the resting form when fitted to the patient to receive an upper arch of the patient in the upper arch receiving channel, and exerts a return force against the received arch to develop the arch form and the base member contributes to generating the resting form return force.

2. An orthodontic appliance according to claim 1, wherein each said complementary pair of upper arch teeth positioning formations is located at a predetermined position along the dental arch form so as to project into a space between two specific adjacent teeth, and the outer and inner teeth positioning formations of each said complementary pair are aligned with each other in a direction transverse to the line of the dental arch form.

3. An orthodontic appliance according to claim 1, wherein each said wedge formation has a substantially vertically extending orientation.

4. An orthodontic appliance according to claim 3, wherein the teeth engaging member, the inner and outer walls, and each said wedge formation are integrally formed with one another of a resiliently deformable material.

5. An orthodontic appliance according to claim 1, wherein the teeth engaging formations include a plurality of complementary pairs of upper arch teeth positioning formations, and the plurality of complementary pairs of upper arch teeth positioning formations are arranged to be bilaterally symmetrical on the teeth engaging member.

6. An orthodontic appliance according to claim 5, wherein the plurality of complementary pairs of upper arch teeth positioning formations includes first and second pairs of complementary teeth positioning formations positioned on opposite sides of a midline of the orthodontic appliance for respectively projecting into the interproximal space positioned between first inner and outer incisors on the left side of the patient and an additional interproximal space positioned between second inner and outer incisors on the right side of the patient.

7. An orthodontic appliance according to claim 5, wherein the plurality of complementary pairs of upper arch teeth positioning formations includes first and second pairs of complementary teeth positioning formations positioned on opposite sides of a midline of the orthodontic appliance for respectively projecting into the interproximal space positioned between a first outer incisor and a first canine on the left side of the patient and an additional interproximal space positioned between a second outer incisor and a second canine on the right side of the patient.

8. An orthodontic appliance according to claim 5, wherein the plurality of complementary pairs of upper arch teeth positioning formations includes first and second pairs of complementary teeth positioning formations positioned on opposite sides of a midline of the orthodontic appliance for respectively projecting into the interproximal space positioned between a first canine and a first pre-molar on the left side of the patient and an additional interproximal space positioned between a second canine and a second pre-molar on the right side of the patient.

9. An orthodontic appliance according to claim 5, wherein the plurality of complementary pairs of upper arch teeth positioning formations includes first and second pairs of complementary teeth positioning formations that are positioned on opposite sides of a midline of the orthodontic appliance for respectively projecting into the interproximal space positioned between a first pre-molar and a first adjacent molar on the left side of the patient and an additional interproximal space positioned between a second pre-molar and a second adjacent molar on the right side of the patient.

10. An orthodontic appliance according to claim 5, wherein the plurality of complementary pairs of upper arch teeth positioning formations includes first and second pairs of complementary teeth positioning formations positioned on opposite sides of a midline of the appliance for respectively projecting into the interproximal space positioned between two adjacent teeth on the left side of the patient and an additional interproximal space positioned between the corresponding two adjacent teeth on the right side of the patient.

11. An orthodontic appliance according to claim 5, wherein the plurality of complementary pairs of upper arch teeth positioning formations includes one complementary pair of teeth engaging formations that are positioned on the midline of the orthodontic appliance for projecting into an the interproximal space positioned between the left and right inner incisors of the patient.

12. An orthodontic appliance according to claim 1, wherein the inner and outer walls of the teeth engaging member project transversely away from a lower surface of the web, and the web and the inner and outer walls define a lower arch receiving channel within which an lower dental arch and associated dentition of the patient can be received, and the orthodontic appliance further includes at least one complementary pair of lower arch teeth positioning formations on the teeth engaging member projecting into the lower arch receiving channel for expanding the lower arch and positioning individual teeth along the lower arch, and each of the lower arch teeth positioning formations comprises a lower arch wedge formation that includes a lower arch wedge base on the inner or outer wall and substantially planar lower arch wedge faces projecting away from the lower arch wedge base to a lower arch wedge apex adapted to project into a lower arch interproximal space between two adjacent lower teeth of the patient when the orthodontic appliance is fitted to the patient.

13. An orthodontic appliance according to claim 12, wherein each said complementary pair of lower arch teeth positioning formations comprises a lower outer teeth positioning formation projecting into the lower arch receiving channel from the outer wall and a lower inner teeth positioning formation projecting into the lower arch receiving channel from the inner wall.

14. An orthodontic appliance according to claim 12, wherein each said complementary pair of lower arch teeth positioning formations is located at a predetermined position along the dental arch form so as to project into a space between two specific adjacent lower teeth, and wherein the lower outer and inner teeth positioning formations of each said complementary pair are aligned with each other in a direction transverse to the line of the dental arch form.

15. An orthodontic appliance according to claim 12, wherein each said lower arch wedge formation has a substantially vertically extending orientation.

16. An orthodontic appliance according to claim 15, wherein each said wedge formation on the lower arch teeth positioning formations is integrally formed with the associated inner or outer wall of the teeth engaging member which is of a resiliently deformable material.

17. An orthodontic appliance according to claim 12, wherein the orthodontic appliance further includes a plurality of complementary pairs of lower arch teeth positioning formations on the teeth engaging member, and the plurality of complementary pairs of lower arch teeth positioning formations are arranged to be bilaterally symmetrical on the teeth engaging member.

18. An orthodontic appliance according to claim 1, wherein the base member includes a frame extending in a plane substantially parallel to the web.

19. A method of treating a patient to develop an underdeveloped mid-facial region of their upper dental arch, said method including:

providing an orthodontic appliance comprising a resiliently deformable teeth engaging member that includes an arch-shaped web that defines upper and lower occlusal bite surfaces, the teeth engaging member has inner and outer walls that project transversely away from the upper surface of the web, and the web and the inner and outer walls define an upper arch receiving channel within which an upper dental arch and associated dentition of a patient can be received, the orthodontic appliance further comprising at least one complementary pair of upper arch teeth positioning formations on the teeth engaging member for expanding the upper dental arch and positioning individual teeth along the upper dental arch, each said complementary pair comprising an outer teeth positioning formation projecting into the upper arch receiving channel from the outer wall and an inner teeth positioning formation projecting into the upper arch receiving channel from the inner wall, each upper arch teeth positioning formation being resiliently deformable and comprising a wedge formation including a wedge base on the inner or outer wall and substantially planar wedge faces projecting away from the wedge base to a wedge apex adapted to project into an interproximal space between two adjacent teeth of the patient when the orthodontic appliance is fitted to the patient, the orthodontic appliance further comprising an arch-shaped base member including a frame extending in a plane parallel to the web that is received within and is substantially enclosed by the teeth engaging member, the base member being formed of a resiliently deformable material having a greater rigidity than the teeth engaging member;

fitting the orthodontic appliance within the mouth of the patient by deforming the orthodontic appliance from a resting form, and mounting the orthodontic appliance over the patient's upper dental arch so that the upper dental arch is received within the upper dental arch receiving channel, and then releasing the deformed orthodontic appliance so that the deformed orthodontic appliance exerts a return force against the upper arch of the patient; and wearing the orthodontic appliance so that the return force against the upper dental arch promotes expansion of the upper dental arch.

20. A method of treating a patient to develop an underdeveloped mid-facial region of their upper dental arch according to claim 19 wherein wearing the orthodontic appliance includes wearing the orthodontic appliance for at least eight hours on substantially each day over a treatment period of 12 to 24 months.

* * * * *